(12) United States Patent
Hanks et al.

(10) Patent No.: US 11,166,799 B2
(45) Date of Patent: Nov. 9, 2021

(54) PHYSIOLOGICAL CONDITION DETERMINATION SYSTEM

(71) Applicant: Maxim Integrated Products, Inc., San Jose, CA (US)

(72) Inventors: John Philip Hanks, Austin, TX (US); Ian Chen, Campbell, CA (US)

(73) Assignee: Maxim Integrated Products, Inc., San José, CA (US)

( * ) Notice: Subject to any disclaimer, the term of this patent is extended or adjusted under 35 U.S.C. 154(b) by 381 days.

(21) Appl. No.: 15/984,169

(22) Filed: May 18, 2018

(65) Prior Publication Data
US 2018/0333244 A1 Nov. 22, 2018

Related U.S. Application Data

(60) Provisional application No. 62/509,006, filed on May 19, 2017, provisional application No. 62/580,389, filed on Nov. 1, 2017.

(51) Int. Cl.
*A61B 5/11* (2006.01)
*A61B 5/00* (2006.01)
(Continued)

(52) U.S. Cl.
CPC .......... *A61D 17/008* (2013.01); *A01K 11/001* (2013.01); *A01K 29/005* (2013.01);
(Continued)

(58) Field of Classification Search
CPC .... A61D 17/008; A61D 17/00; A61B 5/1118; A61B 5/01; A61B 5/02405;
(Continued)

(56) References Cited

U.S. PATENT DOCUMENTS 5,425,362 A * 6/1995 Siker .................... A61B 5/035
600/376
8,273,032 B2 9/2012 Carney et al.
(Continued)

FOREIGN PATENT DOCUMENTS

EP 3430897 A1 * 1/2019 ............. A01K 11/00

OTHER PUBLICATIONS

Grognet (Bloat (or GDV) in Dogs—What It Is and How it's Treated, AKC Website, Nov. 2016 (Year: 2016).*
Verhoeven et al., "Pulse-oximetry accurately predicts lung pathology and the immune response during influenza infection", dated Aug. 1, 2010, https://www.ncbi.nlm.nih.gov/pmc/articles/PMC2776688/.
(Continued)

*Primary Examiner* — Jacqueline Cheng
*Assistant Examiner* — Tho Q Tran
(74) *Attorney, Agent, or Firm* — Robert Crownover

(57) ABSTRACT

A physiological condition determination system and method can include: attaching a tag to animal tissue; emitting light into the animal tissue; detecting a first optical signal; extracting a first measurement of peripheral capillary oxygen saturation from the first optical signal; qualifying the first measurement of peripheral capillary oxygen saturation as a baseline; detecting a second optical signal with the optical sensor; extracting a second measurement of peripheral capillary oxygen saturation from the second optical signal; qualifying the second measurement of peripheral capillary oxygen saturation; storing the second measurement of peripheral capillary oxygen saturation as a tag feature set; storing a history; determining animal distress based on the difference between the second measurement of peripheral capillary oxygen saturation and the baseline; and sending an instruction to the tag.

20 Claims, 12 Drawing Sheets

(51) Int. Cl.
| | |
|---|---|
| *A61B 5/0205* | (2006.01) |
| *A01K 11/00* | (2006.01) |
| *A01K 29/00* | (2006.01) |
| *A61B 5/1455* | (2006.01) |
| *A61B 5/01* | (2006.01) |
| *A61B 5/024* | (2006.01) |
| *A61B 5/08* | (2006.01) |
| *A61D 17/00* | (2006.01) |

(52) U.S. Cl.
CPC ............. *A61B 5/0022* (2013.01); *A61B 5/01* (2013.01); *A61B 5/02055* (2013.01); *A61B 5/02405* (2013.01); *A61B 5/1112* (2013.01); *A61B 5/1118* (2013.01); *A61B 5/14552* (2013.01); *A61B 5/6815* (2013.01); *A61B 5/721* (2013.01); *A61B 5/7278* (2013.01); *A61B 5/7282* (2013.01); *A61B 5/746* (2013.01); *A61D 17/00* (2013.01); *A61B 5/02416* (2013.01); *A61B 5/08* (2013.01); *A61B 5/6839* (2013.01); *A61B 2503/40* (2013.01); *A61B 2560/0242* (2013.01); *A61B 2560/0443* (2013.01); *A61B 2560/0462* (2013.01); *A61B 2562/0271* (2013.01)

(58) Field of Classification Search
CPC ... A61B 5/1112; A61B 5/721; A61B 5/02055; A61B 5/7282; A61B 5/746; A61B 5/0022; A61B 5/7278; A61B 5/6815; A61B 5/14552; A61B 5/02416; A61B 5/6839; A61B 2560/0242; A61B 5/08; A61B 2503/40; A61B 2560/0443; A61B 2560/0462; A61B 2562/0271; A61B 5/0015; A61B 5/0059; A61B 5/0205; A61B 5/024; A61B 5/14551; A01K 11/001; A01K 29/005; G06Q 50/02
USPC ........................................................ 600/304
See application file for complete search history.

(56) References Cited

U.S. PATENT DOCUMENTS

| | | | | |
|---|---|---|---|---|
| 8,909,330 | B2 | 12/2014 | McCombie et al. | |
| 2002/0010390 | A1* | 1/2002 | Guice | A61D 17/002 600/300 |
| 2003/0205208 | A1* | 11/2003 | Bar-Shalom | A01K 29/005 119/859 |
| 2004/0019289 | A1* | 1/2004 | Ross | A61B 5/02405 600/519 |
| 2008/0312511 | A1* | 12/2008 | Osler | G16H 40/67 600/300 |
| 2011/0177184 | A1* | 7/2011 | Suzuki | A61P 3/00 424/776 |
| 2011/0217389 | A1* | 9/2011 | Preuss | A61P 43/00 424/655 |
| 2013/0139817 | A1* | 6/2013 | von Blumenthal | A61M 16/024 128/204.23 |
| 2014/0180027 | A1* | 6/2014 | Buller | A61B 5/01 600/301 |
| 2016/0041217 | A1* | 2/2016 | Lee | G01R 31/58 702/58 |
| 2017/0013802 | A1* | 1/2017 | Zimmerman | G06K 7/10009 |
| 2017/0156288 | A1* | 6/2017 | Singh | A01K 11/004 |
| 2017/0228627 | A1* | 8/2017 | Geissler | G06K 19/07779 |
| 2017/0303784 | A1* | 10/2017 | Huiku | A61B 5/0402 |
| 2017/0325749 | A1* | 11/2017 | Shah | A61B 5/14546 |
| 2018/0184979 | A1* | 7/2018 | Hanks | A61B 5/14552 |
| 2018/0206455 | A1* | 7/2018 | Thiex | A01K 29/005 |
| 2020/0137983 | A1* | 5/2020 | Nieveen | A01K 5/01 |

OTHER PUBLICATIONS

Li et al., "Digital Health: Tracking Physiomes and Activity Using Wearable Biosensors Reveals Useful Health-Related Information", dated Jan. 12, 2017, published on PLOS Biology.

Ellis et al., "Relationship of the extent of pulmonary lesions to the partial pressure of oxygen and the lactate concentration in arterial blood in calves experimentally infected with bovine respiratory syncytial virus", Jul. 2013, https://www.ncbi.nlm.nih.gov/pmc/articles/PMC3700446/#!po=40.1786.

Christine Whitten MD, "What's the Difference Between Oxygen Saturation and PaO2", Dec. 9, 2015, https://airwayjedi.com/2015/12/09/whats-the-difference-between-oxygen-saturation-and-pao2/.

Soltesova et al., "Blood Gases, Acid-Base Status and Plasma Lactate Concentrations in Calves with Respiratory Diseases", 2015, Acta Veterinaria-Beograd.

Ian Chen, "What's in store for optical biosensors? Part 1", published on EDN Network, dated Oct. 11, 2017.

Ian Chen, "What's in store for optical biosensors? Part 2", published on EDN Network, dated Oct. 26, 2017.

Bjarnason, "Development of Implantable Pulse Oxygen Saturation Meter for Dairy-Cattle Respiratory Monitoring", Jan. 11, 2012, https://dspace.cc.tut.fi/dpub/handle/123456789/24945.

"Livestock and Poultry: World Markets and Trade", Apr. 2017, Foreign Agricultural Service/United States Department of Agriculture (USDA) Office of Global Analysis.

Sidwell et al., "Utilization of Pulse Oximetry for the Study of the Inhibitory Effects of Antiviral Agents on Influenza Virus in Mice", Antimicrobial Agents and Chemotherapy, vol. 36, No. 2, Feb. 1992.

"Peer Reviewed Publications Utilizing the MouseOx(TM) Pulse Oximeter", Starr Life Sciences Corp., Jan. 2011.

"Heat stress in cattle—Know the warnings signs!", Drovers, Jul. 26, 2011, https://www.drovers.com/article/heat-stress-cattle-know-warning-signs.

Alan Newport, "Too Much Protein a Problem With Dairy and Beef Producers", BeefProducer, May 22, 2013, http://www.beefproducer.com/blogs-too-much-protein-problem-dairy-beef-prods-7185.

"5 Common Livestock Illnesses: Symptoms, Treatment and Prevention", Aug. 4, 2014, https://www.nelsonmfg.com/blog/5-common-livestock-illnesses-symptoms-treatment-and-prevention/.

"Bovine Anaemia—Theileria", TheCattleSite, http://www.thecattlesite.com/diseaseinfo/252/bovine-anaemia-theileria/.

Davies et al., "The relationship between body temperature, heart rate and respiratory rate in children.", Sep. 2009, https://www.ncbi.nlm.nih.gov/pubmed/19700579.

Lahav et al., "[The effect of fever on blood oxygen saturation in children]", Mar. 2015, https://www.ncbi.nlm.nih.gov/pubmed/25962244.

Varjavand et al., "The Interactive Oxyhemoglobin Dissociation Curve", Jun. 1, 2000, http://www.ventworld.com/resources/oxydisso/dissoc.html.

"Oxyhemoglobin Dissociation Curve made easy", Respiratory Therapy Cave, Jul. 7, 2010, http://respiratorytherapycave.blogspot.com/2010/07/oxyhemoglobin-dissociation-curve.html.

"Nonin Onyx II Fingertip Pulse Oximeter (SpO2)", https://theinsgroup.com.au/wp-content/uploads/Pulse-Ox-Nonin-Fingertip-Data-Sheet.pdf.

"IHealth Model PO3M Wireless Pulse Oximeter Operation Manual", https://www.telmenow.com/media/wysiwyg/pdfs/iHealth_Pulse_Oximeter_Brochure.pdf.

"Mio Alpha 2 Complete User Guide", https://www.mioglobal.com/docs/mio_alpha2_complete-user-guide_en.pdf.

"Fitbit Surge Fitness Super Watch User Manual Version 1.3", https://staticcs.fitbit.com/content/assets/help/manuals/manual_surge_en_US.pdf.

"Zephyr Performance Systems—BioPatch HP User Guide", by Medtronic, Nov. 29, 2016, https://www.zephyranywhere.com/media/download/biopatch-device-user-manual.pdf.

"Owlet", http://apps.showstoppers.com/presskits//ShowStoppers%20CES%20%202017%20press%20kit/Owlet/Owlet%20Fact%20Sheet.pdf.

"Empatica E4", Nov. 19, 2014, http://box.empatica.com/documentation/20141119_E4_TechSpecs.pdf.

(56) References Cited

OTHER PUBLICATIONS

"Helo LX User Guide", https://website.worldgn.com/wp-content/uploads/2017/04/MANUALE-HELO-ENGLISH.pdf.
"AFE4490 Integrated Analog Front-End for Pulse Oximeters", by Texas Instruments Incorporated, Dec. 2012 (revised Oct. 2014), http://www.ti.com/lit/ds/symlink/afe4490.pdf.
"Ultralow Noise, Low Power Current Amplifier—ADPD2210 Data Sheet", by Analog Devices, Inc., Oct. 2015 (revised Dec. 2015), http://www.analog.com/media/en/technical-documentation/data-sheets/ADPD2210.pdf.
"MD300 C63 Pulse Oximeter", by Maxtec, http://www.aesol.com/manuals/MD300C63-DataSheet.pdf.
"CMS5ODL Pulse Oximeter User Manual", by Contec Medical Systems Co., Ltd., http://www.amperorblog.com/doc-lib/CMS50DL.pdf.

\* cited by examiner

PHYSIOLOGICAL CONDITION DETERMINATION SYSTEM

TECHNICAL FIELD

This disclosure relates to physiological monitoring; more particularly, to the determination of physiological conditions using optical sensing methods including, but not limited to, pulse oximetry.

BACKGROUND

Global population growth has given rise to a rapidly increasing demand for livestock. It is becoming increasingly critical that global livestock populations be more carefully managed and controlled to keep pace with ever increasing demand resulting from human population growth.

Of major concern with these livestock populations is their health. In additional to health, there is "well-being" of the livestock. To the livestock farmer, "well-being" turns into "performance" and "productivity" of the animal. Performance for, say, a head of beef cattle is the number of pounds a day it increases in weight. Productivity applies to dairy cows giving milk and chicken laying eggs.

When an animal is stressed or ill, its performance and productivity diminish. Disease and stress can be fatal. Heat stress and bloat, for example, can be fatal to livestock.

Further, disease and infection within the livestock populations can lead to loss of stock and over-reliance on antibiotics; both of which lead to increased costs and loss of competitiveness in the highly commoditized industry.

Illustratively, diseases affecting the cattle population can include bovine respiratory disease, bovine anemia, bloat, and foot and mouth disease. Bovine respiratory disease is the most common and costly disease affecting beef cattle in the world while bovine anemia is a tic-borne disease caused by blood parasites and is spreading into the US.

Diseases cost livestock farmers in the form of mortality and morbidity of the herd. Mortality cost is essentially the opportunity cost of the dead animal plus the cost of the unsuccessful treatments. Morbidity costs are weight loss of the sick animal, failure to gain an optimal amount of weight per day, treatment cost, labor cost in the hospital pen, and cost of missing key market windows.

Bovine respiratory disease is a complex infection that attacks the respiratory system in calves and can be fatal. The infection is usually a sum of multiple codependent factors including stress, an underlying viral infection, and a subsequent bacterial infection.

Bovine respiratory disease often develops within the first 80 days after an animal arrives at a feedlot. The common visible symptoms that bovine respiratory disease causes are indications of depression, such as droopy ears, dull eyes, and social isolation, appetite loss, respiratory distress, and elevated core temperature.

Prevalence of bovine respiratory disease among calves is thought to be around 30%. The costs associated with bovine respiratory disease, in particular, can include decreased growth rate, drug treatments, and mortality.

Previous attempts to mitigate the costs of bovine diseases include visual inspection of the cows. The visual inspections include attempts to identify nasal discharge which appears hours after pyrexia (high temperature), and to identify cough which appears hours after pyrexia. Furthermore, cattlemen on average can only afford to spend fewer than 8 seconds per day observing each animal under their care.

While visual inspections can identify severe cases, many infections in early stages are missed. Visual inspections are labor intensive, subjective, and at best represent a reactionary measure.

Another previous attempt at mitigating the costs of bovine diseases included estimating core body temperature with a temperature probe placed near the tympanic membrane within the ear canal. While true core body temperature measurement is capable of more accurately monitoring and proactively identifying potential infections, estimation accuracies are severely compromised by ambient and placement conditions and installing specialized temperature probes are time consuming, and results in high labor expenses.

Solutions, in terms of early warnings for the onset of disease, event management, and production increases have been long sought but prior developments have not taught or suggested any complete solutions, and solutions to these problems have long eluded those skilled in the art.

Thus, there remains a considerable need for devices and methods that can detect and monitor the health condition of livestock with an industrially viable cost and workflow.

BRIEF DESCRIPTION OF THE DRAWINGS

The determination system is illustrated in the figures of the accompanying drawings which are meant to be exemplary and not limiting, in which like reference numerals are intended to refer to like components, and in which.

DETAILED DESCRIPTION

Figure 1:
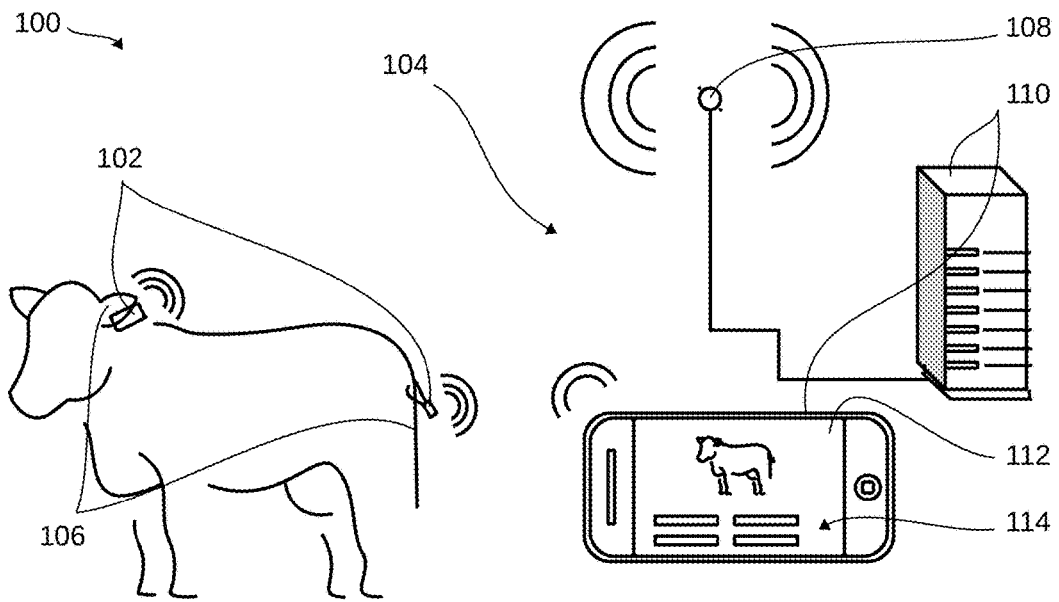
FIG. 1 is a diagrammatic overview of the determination system.

In the following description, reference is made to the accompanying drawings that form a part hereof, and in which are shown by way of illustration, embodiments in which the determination system may be practiced. It is to be understood that other embodiments may be utilized and structural changes may be made without departing from the scope of the determination system.

When features, aspects, or embodiments of the determination system are described in terms of steps of a process, an operation, a control flow, or a flow chart, it is to be understood that the steps can be combined, performed in a different order, deleted, or include additional steps without departing from the determination system as described herein.

The determination system is described in sufficient detail to enable those skilled in the art to make and use the determination system and provide numerous specific details to give a thorough understanding of the determination system; however, it will be apparent that the determination system may be practiced without these specific details.

In order to avoid obscuring the determination system, some well-known configurations and methods are not disclosed in detail. For example, utilizing pulse oximetry in the detection and determination of one or more physiological parameters including but not limited to peripheral capillary oxygen saturation (SpO2), heart rate, heart rate variability, and respiration as well as circuits and systems used to mitigate the effect of ambient light and incidental motion of the system. Likewise, the drawings showing embodiments of the system are semi-diagrammatic and not to scale and, particularly, some of the dimensions are for the clarity of presentation and are shown greatly exaggerated in the drawing FIGS.

For descriptive ease and clarity, the determination system will be described with regard to an implementation with cattle. The disclosure, however, should not be read as limited to or dependent on this implementation and it is contemplated that the determination system could be implemented with any animal where pulse oximetry is applicable, including goats, horses, sheep, swine, poultry, and even humans.

Referring now to FIG. 1, therein is shown a diagrammatic overview of the determination system 100. The determination system 100 is depicted having tags 102 in wireless communication with a network 104.

The tags 102 are shown in physical contact with animal tissue 106. Illustratively, the tags 102 are shown in direct physical contact with an ear and a tail of a cow although it is to be understood that the tags 102 may be attached to other locations and implemented with other animal species.

The network 104 is depicted as a wired and wireless network. The network 104 is shown having antennae 108 for communicating within the network 104 itself and with the tags 102. It is further contemplated that the network 104 could include the antennae 108 for providing wireless power to the tags 102 such as through inductive coupling.

It is contemplated that the network 104 can triangulate the location of the tag 102 using the signal strength of the signals transmitted between the network 104 and the tags 102. In one illustrative example, the network 104 could track the RSSI of the tags 102 and can record the tag 102 and the RSSI of the tag 102 as a location history. As will be appreciated, the location data, or RSSI triangulation of the tags 102 will be understood to be data from the tag communications module 224 of FIG. 2.

Alternatively, the tag 102 could record a network station, such as the antennae 108, and the signal strength of the antennae 108. The strongest antennae along with their associated signal strengths can be stored as location history on the tag 102. It is further contemplated that the strongest antennae 108 along with the next one or more antennae 108 with weaker signal strengths could be stored along with their corresponding signal strengths as the location history in the tag 102.

The network 104 is further shown having computational resources 110 such as servers, computers, and mobile devices. The computational resources 110 are contemplated to include processors and non-transitory computer readable media.

In many such implementations, the network may provide only partial availability. As such, many of the improvements and methods described herein, can improve or mitigate challenges associated with poor network conditions.

The computational resources 110 can include the processors and computer readable media as part of an individual machine or as part of a distributed system including multiple individual devices. The network 104 can be seen to further include a display 112. The display can include the screens of the multiple individual devices or can include a print out. The network 104 can process raw data from the tags 102 into a visual depiction 114 of the animal including metrics, statistics, warnings, and locations on the display 112.

Figure 2:
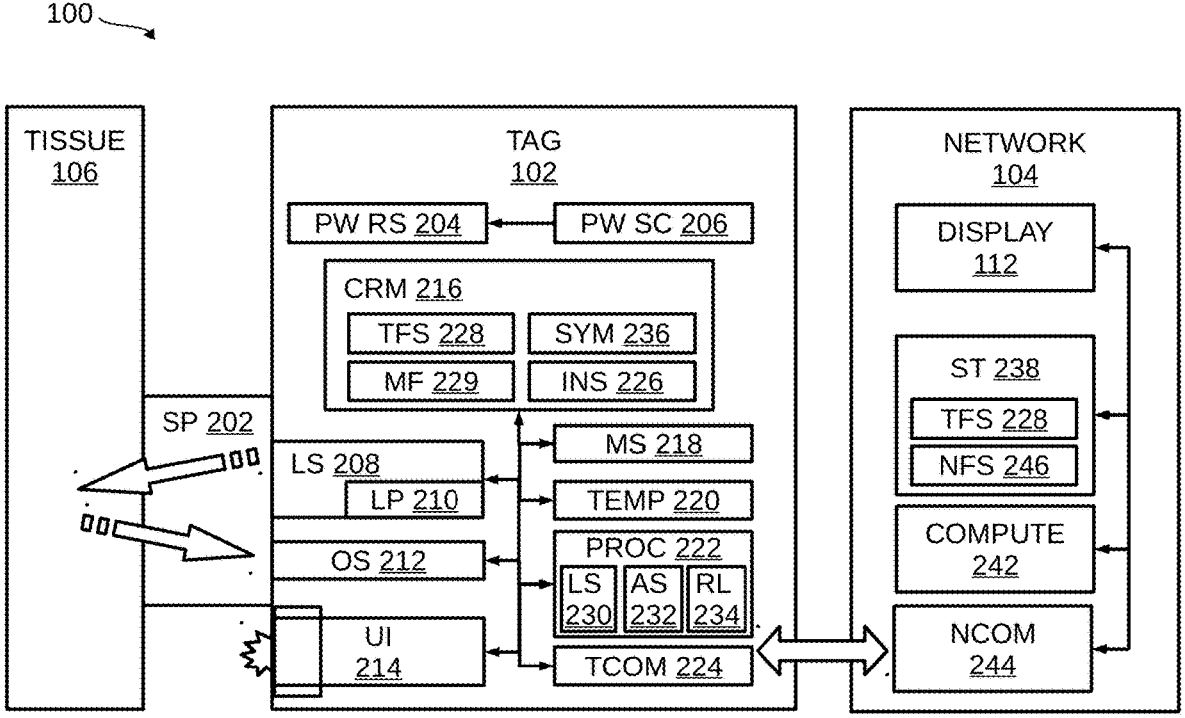
FIG. 2 is a block diagram of the determination system of FIG. 1.

Referring now to FIG. 2, therein is shown a block diagram of the determination system 100 of FIG. 1. The tag 102 is shown to be coupled to the animal tissue 106 with a spacer 202 therebetween. The spacer 202 can be in direct contact with the tag 102 and the animal tissue 106.

It is contemplated that the spacer 202 can have a refractive index identical or substantially similar to that of the animal tissue 106 and can be a polymer based spacer. The spacer 202 is contemplated to be an optional component coupling the animal tissue 106 and the tag 102 and in other implementations the tag 102 can be in direct contact with the animal tissue 106.

The tag 102 is depicted to include a power reservoir 204 such as batteries, capacitors, or a combination thereof. The power reservoir 204 can be coupled to a power source 206 such as a solar power source, inductive wireless power source, or a combination thereof.

The power reservoir 204 or the power source 206 individually or in combination can provide power for the tag 102 including the operation of a light source 208, an optical sensor 212, a user interface 214, a tag computer readable media 216, a motion sensor 218, a thermal sensor 220, processors 222, and a tag communications module 224.

The optical sensor 212 can be one or more optical sensors, light sensors or photodiodes. The light source 208 can consist of one light emitting diode, multiple light emitting diodes, or an array of light emitting diodes. As discussed below, the optical sensor 212 can detect optical data from which heart rate, SpO2, arterial mean pressure, breath rate, and core temperature estimations can be extracted.

The light source 208 may also consist of other light sources alone or in combination with light emitting diodes, and the disclosure is not limited to the utilization of light emitting diodes. Further, the light source 208 can be configured to emit light with various light parameters 210. The light parameters 210 can include one or more wavelengths of light, one or more ranges of wavelengths of light, or a combination thereof.

For example, in one contemplated implementation, the light source 208 can be light emitting diodes emitting light with the light parameters 210 ranging from ultraviolet to infrared. It is contemplated that the species or hide type of the animal will determine the selection of LEDs.

It is further contemplated that the light parameters could include the amplitude of light emitted, the duration of the light pulse, and the sample rate of the light source 208 and the optical sensor 212. The light source 208, the light parameters 210, and the optical sensor 212 can be controlled by the processor 222.

The processor 222 can control the optical sensor 212 and the light source 208 based on an instruction 226 containing the light parameters 210 received by the tag 102 from the network 104. The instruction 226 can be stored in the computer readable media 216 of the tag 102.

The instruction 226 can further include instructions for the general operation of the tag 102 including hibernation or sleep instructions, a requested feature set from the tags, and instructions for processing data streams produced by the optical sensor 212, the motion sensor 218, the thermal sensor 220, and the tag communications module 224.

For example, the motion sensor 218 can be implemented as an accelerometer and can provide a data stream of the change in movement of the tag 102, the thermal sensor 220 can provide a data stream of the ambient temperature around the tag 102, the and the tag communications module 224 can record and detect the closest network 104 antennae 108 or station. The processor 222 can be an embedded processor, a microprocessor, a hardware control logic, a hardware finite state machine, a digital signal processor, or a combination thereof, for example.

The processor 222 can trigger individual LEDs within the light source 208 to emit light in a pulse into the animal tissue 106, which can be absorbed by the animal tissue 106, the oxygenated blood or the deoxygenated blood, or other compounds such as urea contained within the animal tissue 106. The remaining light not absorbed within the animal tissue 106 can be detected by the optical sensor 212. For purposes of this disclosure, remaining light not absorbed by the animal tissue 106 is referred to as residual, or residual light.

The processor 222 can control the timing, sequence, and strength of the LED transmission within the light source 208, based on the instruction 226 sent from the network 104, to ensure the signals detected by the optical sensor 212 are of a known frequency, duration, and strength.

As one example, the processor 222 may be configured by hardware, software or a combination thereof; and, the processor 222 could be configured to control the light parameters 210 for the light emitted from the light source 208. The light parameters 210 can include: frequency, duty cycle, waveform, intensity (e.g., by modulating a magnitude of current or voltage), or a combination thereof. Continuing with the example, it is contemplated that when the light source 208 is implemented as an array of light emitting diodes, the processor 222 can control the light parameters 210 of the light emitted from the light source 208 in each of the individual light emitting diodes within the array.

The processor 222 can further control a user interface 214 based on the instruction 226 sent from the network 104. The user interface 214 can include a signal light emitting diode, alarm speaker, or a combination thereof.

The user interface 214 can be activated on the tag 102 to provide notification and identification that one of the animals has met pre-determined conditions such as having an elevated temperature for over six hours. The pre-determined conditions and thresholds will be discussed in greater detail below with regard to FIG. 9. It is contemplated that the user interface 214 can be activated by the network 104 by sending the instruction 226 to activate the user interface 214 or can be activated by the tag 102 when alert conditions are recognized by the tag 102.

The tag computer readable media 216 can be a non-transitory computer readable media implemented as a volatile memory, a nonvolatile memory, an internal memory, an external memory, or a combination thereof. For example, the tag computer readable media 216 can be a nonvolatile storage such as random access memory, flash memory, disk storage, or a volatile storage such as static random access memory.

The tag computer readable media 216 can buffer the signals detected by the optical sensor 212, the motion sensor 218, the thermal sensor 220, and the tag communications module 224 prior to being transmitted by the tag communications module 224 to the network 104. The tag computer readable media 216 can further include the instructions 226 for the operation and control of the components within the tag 102.

The computer readable media 216 can include tag feature sets 228 and measurement features 229. The tag feature sets 228 along with the measurement features 229 can be qualified data from the optical sensor 212, the motion sensor 218, the thermal sensor 220, and the tag communications module 224, for example.

The measurement features 229 are data representing a physiological characteristic. For example, the measurement features 229 can be the data from the motion sensor 218, the optical sensor 212, the thermal sensor 220, and the tag communications module 224 representing a physiological characteristic, such as photoplethysmogram (PPG), SpO2, heart rate variability, heart rate, respirations, sympathetic nervous system, and others.

It is contemplated, in some implementations, the measurement features 229 can comprise and be identified directly within the raw data of the from the motion sensor 218, the optical sensor 212, the thermal sensor 220, and the tag communications module 224. Alternatively, it is contemplated that the measurement feature 229 could be qualified data, stored as a one part of the tag feature sets 228 and the tag feature sets 228 could be comprised of multiple measurement features 229.

The data or the measurement features 229 from the motion sensor 218, the optical sensor 212, the thermal sensor 220, and the tag communications module 224 can be verified by the processor 222, for example, by analyzing the data therefrom with a longitudinal statistical model 230, an aggregated statistical model 232, data rules 234, or a combination thereof.

Illustratively, the data rules 234 could include a motion qualification for example. Using the motion qualification data rule 234, the tag 102 could collect both optical data from the optical sensor 212 and movement data from the motion sensor 218. If the motion sensor 218 detects any change in movement during the reading of the optical sensor 212, the optical data from the optical sensor 212 could be discarded or discontinued prior to processing the optical signal for extracting features.

As a further illustration, the data rules 234 could include a location qualification for example. Using the location qualification data rule 234, the tag 102 could collect both optical data containing the measurement feature 229 from the optical sensor 212 and location data from the tag communications module 224 in the form of base station triangulation or in the form of recording the closest base stations of the network 104. If the location data indicates that the tag 102 is near a feed trough, for example, the measurement feature 229 of the optical data from the optical sensor 212 can be disregarded or deleted prior to processing because it is known that heart rate, which could be extracted from the optical data of the optical sensor 212, increases due to eating.

It has been discovered that disregarding or deleting the measurement feature 229 of the optical data from the optical sensor 212 prior to processing the optical signal simultaneously reduces power consumption within the tag 102, storage requirements within the tag 102, and communication bandwidth requirements within the tag 102.

The measurement feature 229 of the optical data from the optical sensor 212 can further be qualified by the longitudinal statistical model 230, for example. Illustratively, if SpO2 extracted from the optical data of the optical sensor 212 shows that the current SpO2 level extracted from the optical data is three standard deviations below a historical mean SpO2, the tag 102 could recognize the SpO2 as a statistically significant low SpO2 reading.

The measurement feature 229 of the optical data from the optical sensor 212 can further be qualified by the aggregated statistical model 232, for example. Illustratively, if heart rate extracted from the optical data of the optical sensor 212 shows an increase in the heart rate, which is increasing with a less than two sigma deviation with respect to the heart rates detected by other tags 102 on other animals, the optical data showing the increased heart rate could be disregarded or deleted since the increased heart rate is statistically insignificant with respect to the heart rate data collected from other tags and is therefore likely caused by external factors other than animal health or inflammation.

It is contemplated that the statistical thresholds for the longitudinal statistical model 230 and the aggregated statistical model 232 can be modified based on the implementation of the tag 102 and the quality of the estimate desired. It has been discovered that qualifying the measurement feature 229 of the data from the optical sensor 212, the motion sensor 218, the thermal sensor 220, and the tag communications module 224 simultaneously reduces power requirements, storage requirements, and communication requirements because less computational resources are expended on corrupt data, noisy data, or unimportant data.

The tag 102 can store the data collected from the optical sensor 212, the motion sensor 218, the thermal sensor 220, and the tag communications module 224 and qualified by the longitudinal statistical model 230, the aggregated statistical model 232, and the data rules 234 as the measurement features 229 within the tag feature sets 228. Each of the tag feature sets 228 can include the measurement features 229 representing qualified heart rate, SpO2, arterial mean pressure, breath rate, core temperature estimations extracted from the optical sensor 212.

Each of the tag feature sets 228 can further include the measurement features 229 including qualified motion data from the motion sensor 218, qualified temperature data from the thermal sensor 220, and qualified location information from the tag communications module 224. The tag feature sets 228 can further be timestamped, stored in the computer readable media 216 chronologically, and uploaded to the network 104 chronologically.

The tag feature sets 228 can be encoded into symbols 236 for transmission to the network 104. The symbols 236 or the tag feature sets 228 can be stored on the computer readable media 216 even after transmission of one of the symbols 236 representing the tag feature sets 228 to the network 104 as historical data. For example, it is contemplated that the tag feature sets 228 can be stored on the computer readable media 216 for the previous five days.

It has been discovered that storing multiple days' worth of the tag feature sets 228 can enable the transfer of animals from one lot to another with incompatible networks because the qualified measurement features 229 within the tag feature sets 228 travels with the tag 102. It has further been discovered that storing multiple days' worth of the tag feature sets 228 can enable effective processing with the longitudinal statistical model 230 on the tag 102 itself.

The tag communications module 224 can be a transmitter or a transceiver. For example, it is contemplated the tag communications module 224 can include RFID capabilities and WiFi capabilities for communicating with the network 104. In other examples, the tag communications module 224 can be configured for communication using one or more communications protocols including but not limited to Bluetooth, Bluetooth Low Energy, near field communication (NFC), software defined radio and ad-Hoc WiFi, just to name a few.

The network 104 can include the display 112, storage 238, a computation module 242, and network communications module 244. The display 112 can provide a user interface to set parameters for triggering the user interface 214 of the tag 102, and for monitoring conditions of the livestock.

The storage 238 can be a non-transitory computer readable media implemented as a volatile memory, a nonvolatile memory, an internal memory, an external memory, or a combination thereof. For example, the tag computer readable media 216 can be a nonvolatile storage such as random access memory, flash memory, disk storage, or a volatile storage such as static random access memory.

The storage 238 can be consolidated in a single machine or can be implemented as distributed components. The storage 238 can include instructions configured to operate and control the network 104 and to configure and communicate with the tag 102.

The storage 238 is further depicted as containing the tag feature sets 228 uploaded from the tag 102. The network 104 can use network feature sets 246 stored in the storage 238.

The network feature sets 246 can be qualified data from one or many tags 102. For example, much of the data qualification described above with regard to the data rules 234, the longitudinal statistical model 230, and the aggregated statistical model 232 can be performed on the computation module 242 of the network 104.

It is contemplated that some of the measurement feature 229 qualification processing with the data rules 234, the longitudinal statistical model 230, and the aggregated statistical model 232 may be more effectively performed on the network 104 due to more data available relating to the environment or context of the animals and lower cost of power and processing resources.

The network feature sets 246 are contemplated to include data that the tags 102 do not collect including time of day information to help account for circadian rhythm of the animal affecting the tag data, aggregated herd data, animal transfer data, and dietary data, for example. At the network 104 level, the tag feature sets 228 and the network feature sets 246 can be combined and analyzed using the data rules 234, the longitudinal statistical model 230, and the aggregated statistical model 232.

As an illustrative example, one of the data rules 234 can include discarding data not accompanied by or corresponding with a change in the SpO2 measurement. That is, if the tag 102 transmits the symbol 236 of the tag feature sets 228 including an increase in heart rate without an SpO2 component or without a change in the SpO2 component, the network 104 can disregard or delete the heart rate increase based on the data rules 234. As will also be appreciated, data qualification utilizing the aggregated statistical model 232 can be much more effective when executed on the network 104 since the network 104 can received tag feature sets 228 from multiple tags 102.

The computation module 242 can be an embedded processor, a microprocessor, a hardware control logic, a hardware finite state machine, a digital signal processor, or a combination thereof, for example. The computation module 242 can be localized or part of a distributed computational system.

As will be appreciated, computation and transmission of the raw data streams from the optical sensor 212, the motion sensor 218, the thermal sensor 220, and the tag communications module 224 can be adjusted between the tag 102 and the network 104. For example, as the communications bandwidth decreases the tag 102 can process more of the raw data on the processor 222 prior to sending the symbols 236 to the network 104.

Alternatively, when the tag 102 does not have the processing power or the processor 222 would burn too much energy processing the raw data from the optical sensor 212, the motion sensor 218, the thermal sensor 220, and the tag communications module 224, the computation module 242 in the network 104 can process more of the data than the processor 222.

The network 104 can further include the network communications module 244 for communicating between the network 104 components as well as with the tag 102. The network communications module 244 is contemplated to include the antennae 108 of FIG. 1 as well as other wireless and wired communication components.

It is contemplated that the network 104 can utilize the network communications module 244 to provide a signal through the antenna 108, or a mobile device, for initiating a physiological reading from the light source 208 and the optical sensor 212. In one contemplated example, the network 104 could control the sampling frequency of the tag 102, and the light parameters 210 of the light source 208.

Alternatively, the tag 102 may be configured to operate utilizing default sampling rates and light parameters 210, for example. Yet further, it is contemplated that the tag 102 default sampling rates and light parameters 210 could be initially configured and subsequently modified or changed by the network 104 utilizing the network communications module 244 to provide a signal through the antenna 108, or a mobile device. Illustratively, when the determination system 100 utilizes multiple tags 102, the sampling rates and light parameters 210 for individual tags could be modified by the network 104 to more closely monitor a subset of the livestock.

Figure 3:
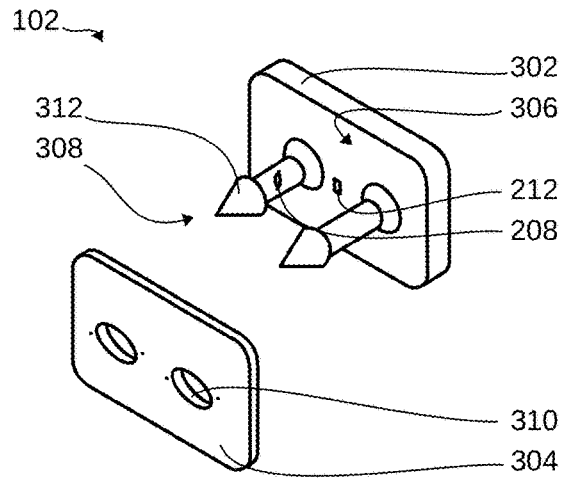
FIG. 3 is an isometric view of the tag of FIG. 1 in a first embodiment.

Referring now to FIG. 3, therein is shown an isometric view of the tag 102 of FIG. 1 in a first embodiment. The tag 102 can include two components including a tag body 302 and a backing plate 304.

The tag body 302 can include a posted side 306 having one or more posts 308 extending therefrom. As will be appreciated, the animal tissue 106 of FIG. 1 can be sandwiched between the tag body 302 and the backing plate 304 with the posts 308 extended through the animal tissue 106 and through holes 310 within the backing plate 304.

The holes 310 can anchor the tag body 302 to the backing plate 304 ensuring solid mechanical contact between the tag body 302 and the animal tissue 106 for providing consistent readings from the optical sensor 212. For example, the posts 308 may include end portions 312 configured to pass through the holes 310 and securely couple the posts 308 to the backing plate 304.

As one example, a diameter of the holes 310 may be less than a diameter or other dimension of the end portions 312 to provide a press or friction fit. The end portions 312, the holes 310, or both may be configured to deform (e.g., be made from a deformable or non-rigid material) as the end portions 312 are pressed through the holes 310, for example.

The tag body 302 can be seen to include the optical sensor 212 and the light source 208. The optical sensor 212 can be positioned on the posted side 306 of the tag body 302.

The light source 208 can be positioned along one of the posts 308. Positioning the light source 208 along one of the posts 308 and the optical sensor 212 on the posted side 306 of the tag body 302 creates a transmissive signal in that a portion of the light emitted by the light source 208 traverses through the animal tissue 106 and is received by (e.g., is incident on) the optical sensor 212.

Although the light source 208 is depicted on the post 308 and the optical sensor 212 depicted on the posted side 306, the optical sensor 212 could be positioned on the post 308 and the light source 208 positioned on the posted side 306 without deviating from the embodiment.

For the purposes of this disclosure when the light source 208 and the optical sensor 212 are positioned on different or multiple surfaces of the tag body 302, the posts 308, or the backing plate 304, the light source 208 and the optical sensor 212 can be understood to be positioned on different surfaces. Illustratively here, the light source 208 is depicted on a surface of the post 308 and the optical sensor 212 is depicted on a surface of the posted side 306, so the light source 208 and the optical sensor 212 can be understood to be positioned on different surfaces.

In some examples, the light source 208 and the optical sensor 212 may be positioned on the same surface or on different surfaces of the posts 308. In other examples, the light source 208 and the optical sensor 212 may be positioned on the same surface or on difference surfaces of the tag body 302 (e.g., on the posted side 306 of the tag body 302). The light source 208 and the optical sensor 212 may be positioned in an aperture, recess, hole, groove, mount, fitting or other structure of the post and/or the posted side.

Figure 4:
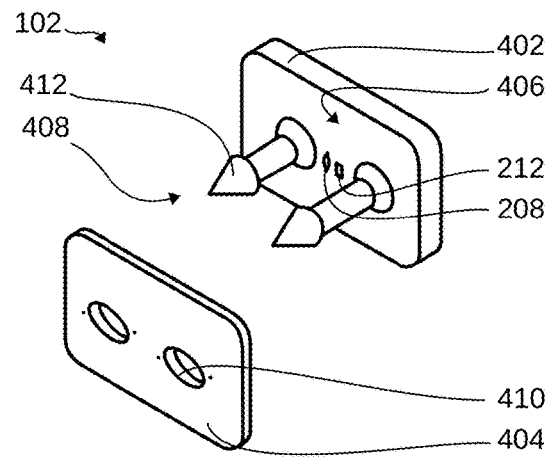
FIG. 4 is an isometric view of the tag of FIG. 1 in a second embodiment.

Referring now to FIG. 4, therein is shown an isometric view of the tag 102 of FIG. 1 in a second embodiment. The tag 102 can include two components including a tag body 402 and a backing plate 404.

The tag body 402 can include a posted side 406 having one or more posts 408 extending therefrom. As will be appreciated, the animal tissue 106 of FIG. 1 can be sandwiched between the tag body 402 and the backing plate 404 with the posts 408 extended through the animal tissue 106 and through holes 410 within the backing plate 404.

The holes 410 can anchor the tag body 402 to the backing plate 404 ensuring solid mechanical contact between the tag body 402 and the animal tissue 106 for providing consistent readings from the optical sensor 212. For example, the posts 408 may include end portions 412 configured to pass through the holes 410 and securely couple the posts 408 to the backing plate 404.

As one example, a diameter of the holes 410 may be less than a diameter or other dimension of the end portions 412 to provide a press or friction fit. The end portions 412, the holes 410, or both may be configured to deform (e.g., be made from a deformable or non-rigid material) as the end portions 412 are pressed through the holes 410, for example.

The tag body 402 can be seen to include the optical sensor 212 and the light source 208. The light source 208 and the optical sensor 212 can be positioned on the posted side 406 of the tag body 402. Positioning the light source 208 and the optical sensor 212 on the posted side 406 of the tag body 402 creates a reflective signal (e.g., light emitted by the light source 208 is reflected and/or scattered by structure within the animal tissue 106) in that a portion of the light emitted by the light source 208 reflects from within the animal tissue 106 and is received by (e.g., is incident on) the optical sensor 212.

Although the light source 208 and the optical sensor 212 are depicted between the posts 408 on the posted side 406, the optical sensor 212 and the light source 208 could be positioned in other locations on the posted side 406 without deviating from the embodiment.

For the purposes of this disclosure when the light source 208 and the optical sensor 212 are both positioned on the same surface of the tag body 402, the posts 408, or the backing plate 404, the light source 208 and the optical sensor 212 can be understood to be positioned on a single surface. Illustratively here, the light source 208 and the optical sensor 212 are depicted as positioned on surface of the posted side 406, so the optical sensor 212 and the light source 208 can be understood to be positioned on a single surface.

Figure 5:
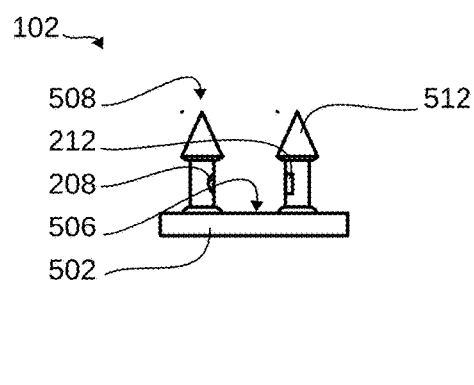
FIG. 5 is a side view of the tag of FIG. 1 in a third embodiment.

Referring now to FIG. 5, therein is shown a side view of the tag 102 of FIG. 1 in a third embodiment. The tag 102 can include a tag body 502.

The tag body 502 can include a posted side 506 having one or more posts 508 extending therefrom. As will be appreciated, the tag 102 can be affixed to the animal tissue 106 of FIG. 1 with the posts 508 extended through the animal tissue 106. It is contemplated that a backing plate may be optionally used for anchoring the tag 102 to the animal tissue 106.

For example, the posts 508 may include end portions 512 configured to pass through holes in a backing plate (not shown) similar to the examples of FIGS. 3 and 4 above. The tag body 502 can be seen to include the optical sensor 212 and the light source 208.

The light source 208 can be positioned along one of the posts 508 while the optical sensor 212 can be positioned along the other post 508. Positioning the light source 208 and the optical sensor 212 on the posts 508 creates a transmissive signal in that a portion of the light emitted by the light source 208 traverses through the animal tissue 106 and is received by (e.g., is incident on) the optical sensor 212.

For the purposes of this disclosure when the light source 208 and the optical sensor 212 are positioned on different or multiple surfaces of the tag body 502 or the posts 508, the light source 208 and the optical sensor 212 can be understood to be positioned on different surfaces. Illustratively here, the light source 208 is positioned on a surface of one of the posts 508 while the optical sensor 212 positioned on a surface of the other post 508, so the optical sensor 212 and the light source 208 can be understood to be positioned on different surfaces.

Figure 6:
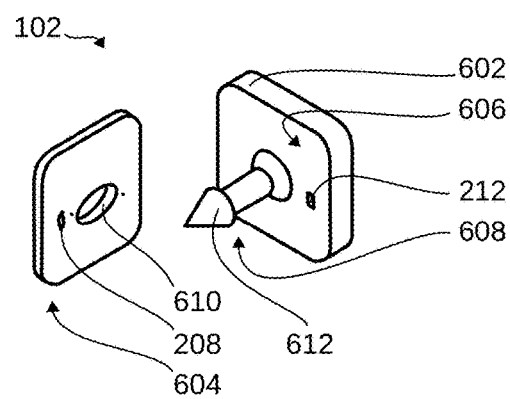
FIG. 6 is an isometric view of the tag of FIG. 1 in a fourth embodiment.

Referring now to FIG. 6, therein is shown an isometric view of the tag 102 of FIG. 1 in a fourth embodiment. The tag 102 can include two components including a tag body 602 and a backing plate 604.

The tag body 602 can include a posted side 606 having a single post 608 extending therefrom. As will be appreciated, the animal tissue 106 of FIG. 1 can be sandwiched between the tag body 602 and the backing plate 604 with the post 608 extended through the animal tissue 106 and through a hole 610 within the backing plate 604.

The hole 610 can anchor the tag body 602 to the backing plate 604 ensuring solid mechanical contact between the tag body 602 and the animal tissue 106 for providing consistent readings from the optical sensor 212. For example, the post 608 may include an end portion 612 configured to pass through the hole 610 and securely couple the post 608 to the backing plate 604.

As one example, a diameter of the hole 610 may be less than a diameter or other dimension of the end portion 612 to provide a press or friction fit. The end portion 612, the hole 610, or both may be configured to deform (e.g., be made from a deformable or non-rigid material) as the end portion 612 is pressed through the holes 610, for example.

The tag body 602 can be seen to include the optical sensor 212 while the light source 208 is depicted as positioned on the backing plate 604. The optical sensor 212 can be positioned on the posted side 606 of the tag body 602 while the light source 208 can be positioned on the backing plate 604 facing the tag body 602. Positioning the light source 208 on the backing plate 604 and the optical sensor 212 on the posted side 606 of the tag body 602 creates a transmissive signal in that a portion of the light emitted by the light source 208 traverses through the animal tissue 106 and is received by (e.g., is incident on) the optical sensor 212.

Although the light source 208 is depicted on the backing plate 604 and the optical sensor 212 depicted on the posted side 606 of the tag body 602, the optical sensor 212 could be positioned on the backing plate 604 and the light source 208 positioned on the posted side 606 without deviating from the embodiment.

For the purposes of this disclosure when the light source 208 and the optical sensor 212 are positioned on different or multiple surfaces of the tag body 602, the post 608, or the backing plate 604, the light source 208 and the optical sensor 212 should be understood to be positioned on different surfaces. Illustratively here, the light source 208 is positioned on a surface of the backing plate 604 and the optical sensor 212 positioned on a surface of the posted side 606 of the tag body 602, so the light source 208 and the optical sensor 212 can be understood to be positioned on different surfaces.

Figure 7:
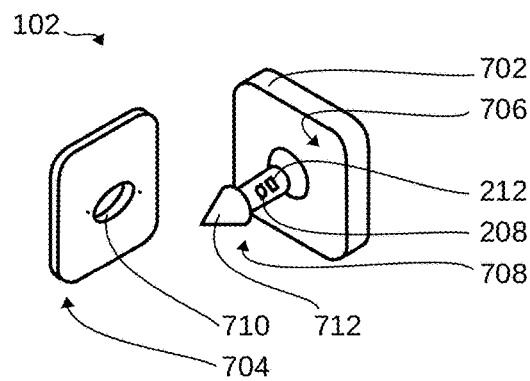
FIG. 7 is an isometric view of the tag of FIG. 1 in a fifth embodiment.

Referring now to FIG. 7, therein is shown an isometric view of the tag 102 of FIG. 1 in a fifth embodiment. The tag 102 can include two components including a tag body 702 and a backing plate 704.

The tag body 702 can include a posted side 706 having a single post 708 extending therefrom. As will be appreciated, the animal tissue 106 of FIG. 1 can be sandwiched between the tag body 702 and the backing plate 704 with the post 708 extended through the animal tissue 106 and through a hole 710 within the backing plate 704.

The hole 710 can anchor the tag body 702 to the backing plate 704 ensuring solid mechanical contact between the tag body 702 and the animal tissue 106 for providing consistent readings from the optical sensor 212. For example, the post 708 may include an end portion 712 configured to pass through the hole 710 and securely couple the post 708 to the backing plate 704.

As one example, a diameter of the hole 710 may be less than a diameter or other dimension of the end portion 712 to provide a press or friction fit. The end portion 712, the hole 710, or both may be configured to deform (e.g., be made from a deformable or non-rigid material) as the end portion 712 is pressed through the holes 710, for example.

The post 708 can be seen to include both the optical sensor 212 and the light source 208 positioned along the post 708. Positioning the light source 208 and the optical sensor 212 on the post 708 creates a reflective signal (e.g., light emitted by the light source 208 is reflected and/or scattered by structure within the animal tissue 106) in that a portion of the light emitted by the light source 208 reflects from within the animal tissue 106 and is received by (e.g., is incident on) the optical sensor 212.

For the purposes of this disclosure when the light source 208 and the optical sensor 212 are both positioned on the same surface of the tag body 702, the post 708, or the backing plate 704, the light source 208 and the optical sensor 212 can be understood to be positioned on a single surface. Illustratively here, the optical sensor 212 and the light source 208 are shown positioned on a surface of the post 708, so the light source 208 and the optical sensor 212 can be understood to be positioned on a single surface.

Figure 8:
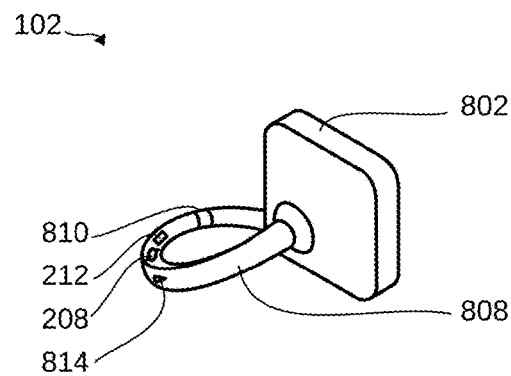
FIG. 8 is an isometric view of the tag of FIG. 1 in a sixth embodiment.

Referring now to FIG. 8, therein is shown an isometric view of the tag 102 of FIG. 1 in a sixth embodiment. The tag 102 can include a tag body 802 and a loop 808. The loop 808 is depicted extending from one side of the tag body 802 into an opposite side of the tag body 802.

As will be appreciated, the loop 808 can be extended through the animal tissue 106 of FIG. 1, for example, as a loop or hook through the tail of an animal. The loop 808 can include a connecting junction 810 for connecting two portions of the loop 808 together.

Illustratively, it is contemplated that the loop 808 can be opened at the connecting junction 810, extended through the animal tissue 106 and then closed again using the connecting junction 810. The loop 808 can be seen to include both the optical sensor 212 and the light source 208 positioned along the loop 808.

The loop 808 is further shown having a temperature sensor 814. It is contemplated that when the tag 102 implementing the loop 808 is positioned on the tail of an animal, the temperature sensor 814 can take peripheral temperature measurements near the anus of the animal.

Positioning the light source 208 and the optical sensor 212 on the loop 808 creates a reflective signal (e.g., light emitted by the light source 208 is reflected and/or scattered by structure within the animal tissue 106) in that a portion of the light emitted by the light source 208 reflects from within the animal tissue 106 and is received by (e.g., is incident on) the optical sensor 212.

For the purposes of this disclosure when the light source 208 and the optical sensor 212 are both positioned on the same surface of the tag body 802 or the loop 808, the light source 208 and the optical sensor 212 can be understood to be positioned on a single surface. Illustratively here, the optical sensor 212 and the light source 208 are shown positioned on a surface of the loop 808, so the light source 208 and the optical sensor 212 can be understood to be positioned on a single surface.

Figure 9:
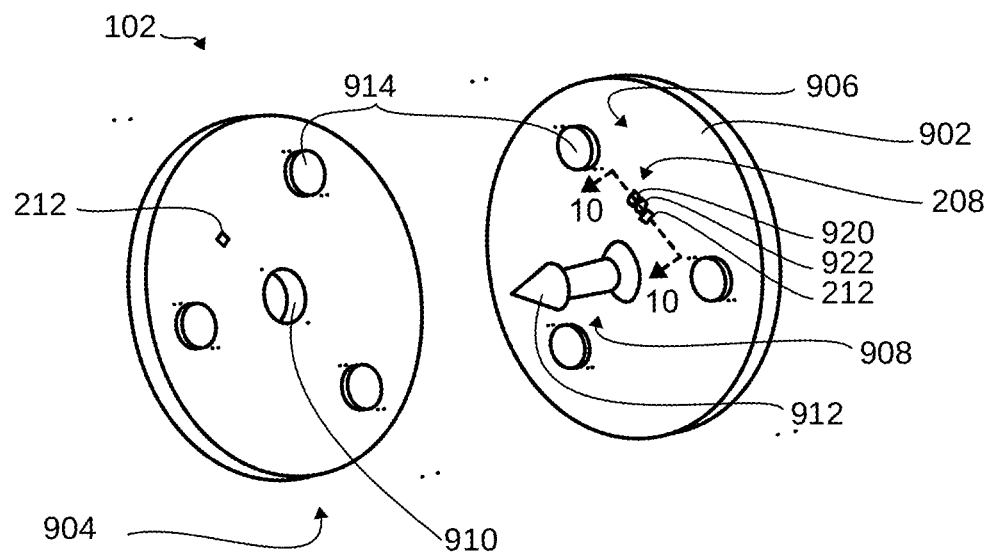
FIG. 9 is an isometric view of the tag of FIG. 1 in a seventh embodiment.

Referring now to FIG. 9, therein is an isometric view of the tag 102 of FIG. 1 in a seventh embodiment. The tag 102 can include two components including a tag body 902 and a backing plate 904.

The tag body 902 can include a posted side 906 having a single post 908 extending therefrom while the backing plate 904 can include a hole 910 therethrough. The post 908 can include an end portion 912. The end portion 912 can be a conical point configured to pass through the animal tissue 106 of FIG. 1 and through the hole 910 of the backing plate 904.

Solid mechanical contact between the tag body 902, the backing plate 904 and the animal tissue 106 therebetween, can be ensured by the interference fit of the post 908 extending through and contacting the hole 910. Solid mechanical contact between the tag body 902, the backing plate 904 and the animal tissue 106 therebetween, can further be ensured by the physical contact between the hole 910 and the end portion 912 when inserted through the hole 910.

As one example, a diameter of the hole 910 may be less than a diameter or other dimension of the end portion 912 to provide a press or friction fit. The end portion 912, the hole 910, or both may be configured to deform (e.g., be made from a deformable or non-rigid material) as the end portion 912 is pressed through the holes 910, for example.

The backing plate 904 and the tag body 902 are further depicted to include magnets 914. The magnets 914 can be positioned on the backing plate 904 and the tag body 902 to ensure that only one rotational position of the backing plate 904 and tag body 902 will result in alignment between the magnets 914 on the backing plate 904 and the magnets 914 on the tag body 902; thus, ensuring alignment between the optical sensor 212 on the backing plate 904 and the light sources 208.

Solid mechanical contact between the tag body 902, the backing plate 904 and the animal tissue 106 therebetween, can be ensured by the pull between the magnets 914 on the backing plate 904 and the magnets 914 on the tag body 902. The solid mechanical contact between the tag body 902, the backing plate 904, and the animal tissue 106 therebetween, can be important in providing consistent readings from the optical sensors 212.

The tag body 902 can be seen to include another one of the optical sensors 212 and the light sources 208. It will be appreciated that the optical sensor 212 positioned on the backing plate 904 can provide a transmissive signal in that a portion of the light emitted by the light sources 208 traverses through the animal tissue 106 and is received by (e.g., is incident on) the optical sensor 212 on the backing plate 904.

On the other hand, the optical sensor 212 positioned on the tag body 902 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the tag body 902.

For the purposes of this disclosure when the light sources 208 and the optical sensors 212 are both positioned on the same surface of the tag body 902, the post 908, or the backing plate 904, the light sources 208 and the optical sensors 212 can be understood to be positioned on a single surface. Illustratively here, the optical sensor 212 on the tag body 902 and the light sources 208 are shown positioned on a posted side 906 of the tag body 902 and can be understood to be positioned on a single surface. In some examples, the optical sensor 212 and the light source 208 may be positioned on a surface of the post 908 (not shown), so the light source 208 and the optical sensor 212 can be understood to be positioned on a single surface (e.g., see light source 208 and optical sensor 212 positioned on a single surface of post 708 in FIG. 7).

The light sources 208 can include multiple sources of light for various measurements. For example, the light sources 208 can include a red to infrared source 920. The red to infrared source 920 can be utilized to determine or measure peripheral blood oxygen saturation based on the absorption characteristics of the red to infrared light emitted from the red to infrared source 920.

The light sources 208 can further include an ultraviolet source 922, for example. The ultraviolet source 922 can be utilized to determine the concentrations of blood urea based on the absorption characteristics of the ultraviolet light emitted from the ultraviolet source 922.

Figure 10:
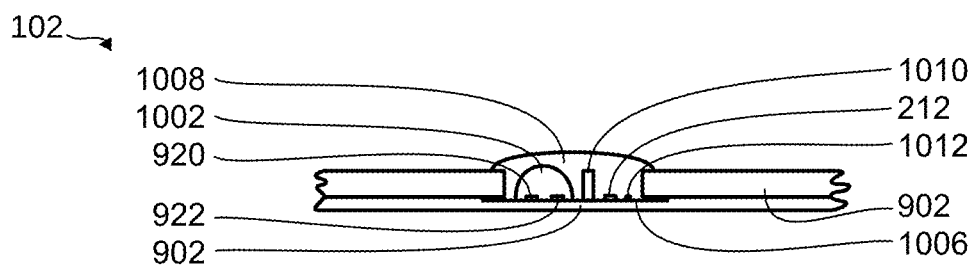
FIG. 10 is a cross-sectional view of the tag of FIG. 9 along the line 10-10 of FIG. 9.

Referring now to FIG. 10, therein is shown a cross-sectional view of the tag 102 of FIG. 9 along the line 10-10 of FIG. 9. The light sources 208 of FIG. 2 are shown as the infrared source 920 and the ultraviolet source 922.

The infrared source 920 and the ultraviolet source 922 are depicted exposed from the tag body 902. A first sealant 1002 is shown covering the infrared source 920 and the ultraviolet source 922 above a printed circuit board 1006. The first sealant 1002 can be the spacer 202 of FIG. 2.

The light sources 208 as well as the optical sensor 212 can be mounted to the printed circuit board 1006. The first sealant 1002 can extend from the printed circuit board 1006 over the optical sensors 212 to extend above a top surface of the tag body 902.

The first sealant 1002 can be a polymer or a silicon based sealant for protecting sensitive electronics from external or environmental stresses. It is contemplated that the first sealant 1002 can have an index of refraction of between 1.3 and 1.4, which approximates that of the animal tissue 106 of FIG. 1.

A second sealant 1008 can be formed on the printed circuit board 1006 for encapsulating the first sealant 1002, the optical sensor 212, and the light sources 208. The second sealant 1008 could similarly be a polymer or a silicon based sealant for protecting sensitive electronics from external or environmental stresses, and the second sealant 1008 can have an index of refraction of between 1.3 and 1.4, which approximates that of the animal tissue 106. The second sealant 1008 can be the spacer 202.

The tag body 902 is shown below and above the printed circuit board 1006. The second sealant 1008 can be seen in direct contact with vertical sides of the tag body 902, a barrier 1010 between the light source 208 and the optical sensors 212, the light source 208, and the first sealant 1002.

Next to the optical sensor 212, a pressure sensor 1012 can be mounted to the printed circuit board 1006. The pressure sensor 1012 can be a piezoelectric sensor, or a micro mechanical sensor. It is further contemplated that the pressure sensor 1012 can be a pressure sensitive coating, or a pressure sensitive seal.

It has been discovered that ensuring proper fit of the tag 102 on livestock can be a challenge in an environment where data collection is a secondary consideration. To this end, the pressure sensor 1012 can provide an indication that proper contact is being made between the tag 102 and the animal tissue 106. As will be appreciated, proper contact between the animal tissue 106 and the tag 102 can be seen as a prerequisite for collecting proper data.

Figure 11:
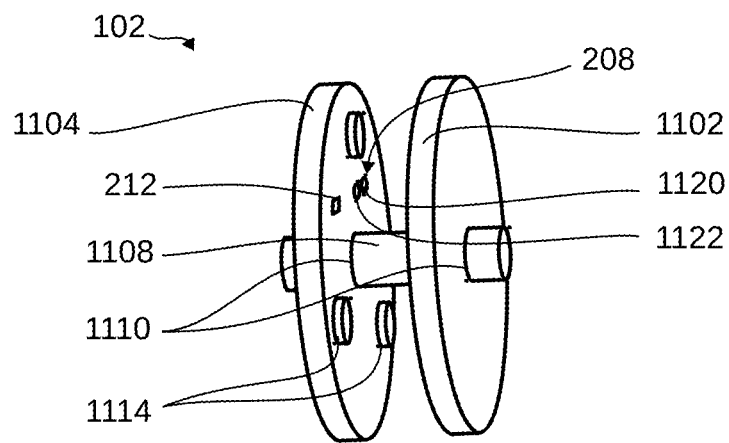
FIG. 11 is an isometric view of the tag of FIG. 1 in an eighth embodiment.

Referring now to FIG. 11, therein is an isometric view of the tag 102 of FIG. 1 in an eighth embodiment. The tag 102 can include two components including a tag body 1102 and a backing plate 1104.

A post 1108 can extend through holes 1110 within the tag body 1102 and the backing plate 1104. The backing plate 1104 and the tag body 1102 can slide along the post 1108 toward and away from one another.

The post 1108 is depicted having a consistent cross section allowing the backing plate 1104 and the tag body 1102 to slide off of the post. It is contemplated that alternative embodiments can include widened ends of the post 1108 allowing containment of the tag body 1102 and the backing plate 1104 on the post 1108 or can include pins, plates, or other components to prohibit the backing plate 1104 or the tag body 1102 from sliding off of the post 1108.

Solid mechanical contact between the tag body 1102, the backing plate 1104 and the animal tissue 106 of FIG. 1 therebetween, can be ensured by the interference or friction fit of the post 1108 extending through and contacting the holes 1110 on both the backing plate 1104 and the tag body 1102. The backing plate 1104 is further depicted to include magnets 1114.

The magnets 1114 can be positioned on the backing plate 1104 and the tag body 1102 to ensure that only one rotational position of the backing plate 1104 and tag body 1102 will result in alignment between the magnets 1114 on the backing plate 1104 and the magnets 1114 on the tag body 1102.

Solid mechanical contact between the tag body 1102, the backing plate 1104 and the animal tissue 106 therebetween, can also be ensured by the pull between the magnets 1114 on the backing plate 1104 and the magnets 1114 on the tag body 1102. The solid mechanical contact between the tag body 1102, the backing plate 1104, and the animal tissue 106 therebetween, can be important in providing consistent readings from the optical sensors 212.

It has been discovered that in some embodiments when the animal tissue 106 has sufficiently large blood vessels, such as with cattle, the tag 102 need not puncture through the animal tissue 106. Rather, effective readings can be achieved with firm pressure providing direct contact between the tag 102 and the animal tissue 106; for example, by way of friction fittings, magnets, springs, or a combination thereof.

The backing plate 1104 can include the optical sensors 212 and the light sources 208. It will be appreciated that the optical sensor 212 positioned on the backing plate 1104 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the tag body 1102.

For the purposes of this disclosure when the light sources 208 and the optical sensors 212 are both positioned on the same surface of the tag body 1102, the post 1108, or the backing plate 1104, the light sources 208 and the optical sensors 212 can be understood to be positioned on a single surface. Illustratively here, the optical sensor 212 and the light sources 208 are shown positioned on a single surface of the backing plate 1104.

The light sources 208 can include multiple sources of light for various measurements. For example, the light sources 208 can include a red to infrared source 1120. The red to infrared source 1120 can be utilized to determine or measure peripheral blood oxygen saturation based on the absorption characteristics of the red to infrared light emitted from the red to infrared source 1120.

The light sources 208 can further include an ultraviolet source 1122, for example. The ultraviolet source 1122 can be utilized to determine the concentrations of blood urea based on the absorption characteristics of the ultraviolet light emitted from the ultraviolet source 1122.

Figure 12:
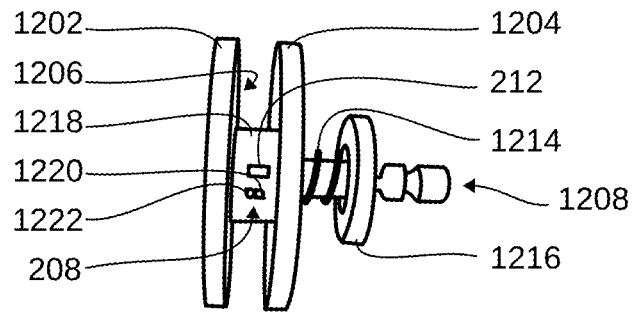
FIG. 12 is a side view of the tag of FIG. 1 in a ninth embodiment.

Referring now to FIG. 12, therein is a side view of the tag 102 of FIG. 1 in a ninth embodiment. The tag 102 can include two components including a tag body 1202 and a backing plate 1204.

The tag body 1202 can include a posted side 1206. The posted side 1206 can provide a post 1208 extending therefrom. The post 1208 can extend away from the posted side 1206 and extend through a hole in the backing plate 1204.

The backing plate 1204 can slide along the post 1208 toward and away from the tag body 1202. A spring 1214 can provide a compressive force against the backing plate 1204 by forcing the backing plate 1204 toward the tag body 1202.

The spring 1214 can be compressed between the backing plate 1204 and an anchor plate 1216, for example. The anchor plate 1216 can extend from and orthogonally to the post 1208.

The spring 1214 can force the backing plate 1204 toward the tag body 1202 and can be stopped by a spacer 1218 between the backing plate 1204 and the tag body 1202. It is contemplated that the spacer 1218 can be integrally formed with the tag body 1202, the backing plate 1204, the post 1208, or a combination thereof.

The spacer 1218 can be designed, for example, to provide proper spacing between the tag body 1202 and the backing plate 1204 based on the type and location of the animal tissue 106 of FIG. 1 to be contacted. The spring 1214 can provide solid mechanical contact between the tag body 1202, the backing plate 1204 and the animal tissue 106 therebetween. The solid mechanical contact between the tag body 1202, the backing plate 1204, and the animal tissue 106 therebetween, can be important in providing consistent readings from the optical sensors 212.

It has been discovered that in some embodiments when the animal tissue 106 has sufficiently large blood vessels, such as with cattle, the tag 102 need not puncture through the animal tissue 106. Rather, effective readings can be achieved with firm pressure providing direct contact between the tag 102 and the animal tissue 106; for example, by way of friction fittings, magnets, springs, or a combination thereof.

The spacer 1218 can include the optical sensor 212 and the light sources 208. It will be appreciated that the optical sensor 212 positioned on the spacer 1218 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the spacer 1218.

For the purposes of this disclosure when the light sources 208 and the optical sensors 212 are both positioned on the same surface of the tag body 1202, the post 1208, the backing plate 1204, or the spacer 1218, the light sources 208 and the optical sensors 212 can be understood to be positioned on a single surface. Illustratively here, the optical sensor 212 and the light sources 208 are shown positioned on a single surface of the spacer 1218.

The light sources 208 can include multiple sources of light for various measurements. For example, the light sources 208 can include a red to infrared source 1220. The red to infrared source 1220 can be utilized to determine or measure peripheral blood oxygen saturation based on the absorption characteristics of the red to infrared light emitted from the red to infrared source 1220.

The light sources 208 can further include an ultraviolet source 1222, for example. The ultraviolet source 1222 can be utilized to determine the concentrations of blood urea based on the absorption characteristics of the ultraviolet light emitted from the ultraviolet source 1222.

Figure 13:
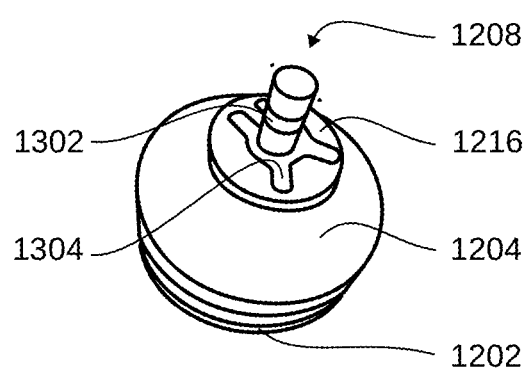
FIG. 13 is an isometric view of the tag of FIG. 12.

Referring now to FIG. 13, therein is an isometric view of the tag 102 of FIG. 12. The backing plate 1204 is shown between the tag body 1202 and the anchor plate 1216.

The post 1208 is shown extending through the anchor plate 1216. The post 1208 can include grooves 1302 formed therein.

The grooves 1302 can provide better grip for a user and can further be used to secure a retaining clip 1304. The retaining clip 1304 can provide a back stop along the post 1208 for the anchor plate 1216 ensuring the anchor plate 1216 does not move farther away from the tag body 1202 due to the force of the spring 1214 of FIG. 12. The retaining clip 1304 can be secured within one of the grooves 1302 of the post 1208 through an open end which can include friction fit or spring properties enabling the retaining clip 1304 to be secured to the post 1208.

Figure 14:
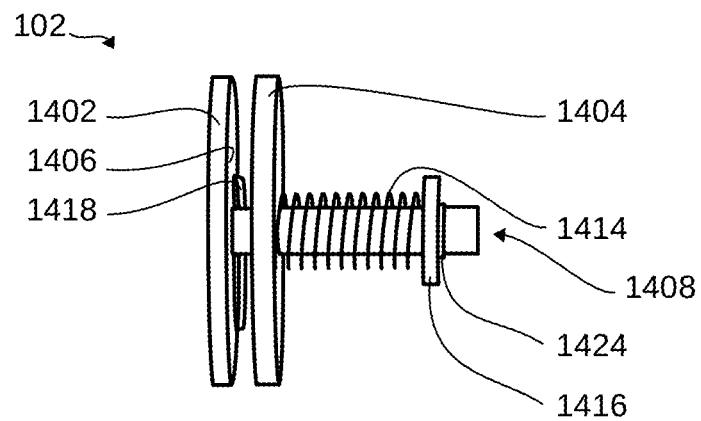
FIG. 14 is a side view of the tag of FIG. 1 in a tenth embodiment.

Referring now to FIG. 14, therein is a side view of the tag 102 of FIG. 1 in a tenth embodiment. The tag 102 can include two components including a tag body 1402 and a backing plate 1404.

The tag body 1402 can include a posted side 1406. The posted side 1406 can provide a post 1408 extending therefrom. The post 1408 can extend away from the posted side 1406 and extend through a hole in the backing plate 1404.

The backing plate 1404 can slide along the post 1408 toward and away from the tag body 1402. A spring 1414 can provide a compressive force against the backing plate 1404 by forcing the backing plate 1404 toward the tag body 1402.

The spring 1414 can be compressed between the backing plate 1404 and an anchor plate 1416, for example. The anchor plate 1416 can extend from and orthogonally to the post 1408.

A retaining clip 1424 can provide a back stop along the post 1408 for the anchor plate 1416 ensuring the anchor plate 1416 does not move farther away from the tag body 1402 due to the force of the spring 1414. The retaining clip 1424 can be secured within grooves along the post 1408 through an open end which can include friction fit or spring properties enabling the retaining clip 1424 to be secured to the post 1408.

The spring 1414 can force the backing plate 1404 toward the tag body 1402 and can be stopped by a spacer 1418 between the backing plate 1404 and the tag body 1402. It is contemplated that the spacer 1418 can be integrally formed with the tag body 1402, for example.

The spacer 1418 can be designed, for example, to provide proper spacing between the tag body 1402 and the backing plate 1404 based on the type and location of the animal tissue 106 of FIG. 1 to be contacted. The spring 1414 can provide solid mechanical contact between the tag body 1402, the backing plate 1404 and the animal tissue 106 therebetween. The solid mechanical contact between the tag body 1402, the backing plate 1404, and the animal tissue 106 therebetween, can be important in providing consistent readings from the optical sensors 212 of FIG. 2.

It has been discovered that in some embodiments when the animal tissue 106 has sufficiently large blood vessels, such as with cattle, the tag 102 need not puncture through the animal tissue 106. Rather, effective readings can be achieved with firm pressure providing direct contact between the tag 102 and the animal tissue 106; for example, by way of friction fittings, magnets, springs, or a combination thereof.

It is contemplated that the optical sensor 212 and the light sources 208 of FIG. 2 can be positioned within or below the spacer 1418, for example, and can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the tag body 1402.

For the purposes of this disclosure when the light sources 208 and the optical sensors 212 are both positioned on the same surface of the tag body 1402, the post 1408, the backing plate 1404, or the spacer 1418, the light sources 208 and the optical sensors 212 can be understood to be positioned on a single surface. Illustratively here, the optical sensor 212 and the light sources 208 are positioned on a single surface of the tag body 1402.

The light sources 208 can include multiple sources of light for various measurements. For example, the light sources 208 can include a red to infrared source for determining or measuring peripheral blood oxygen saturation based on the absorption characteristics of the red to infrared light. The light sources 208 can further include an ultraviolet source for determining the concentrations of blood urea based on the absorption characteristics of the ultraviolet light.

Figure 15:
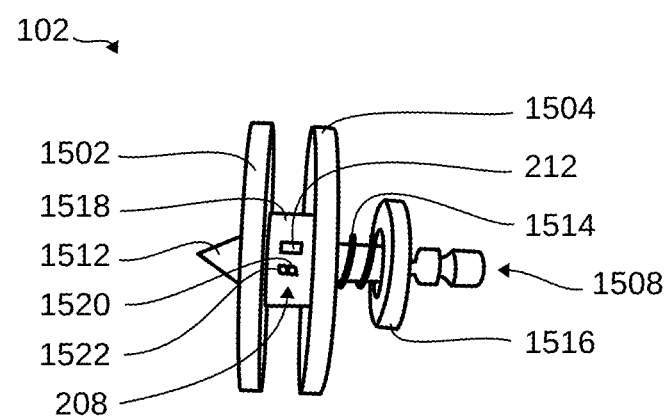
FIG. 15 is a side view of the tag of FIG. 1 in an eleventh embodiment.

Referring now to FIG. 15, therein is a side view of the tag 102 of FIG. 1 in an eleventh embodiment. The tag 102 can include two components including a tag body 1502 and a backing plate 1504.

A post 1508, having an end portion 1512, can extend through holes within the tag body 1502 and the backing plate 1504. The end portion 1512 can securely couple the post 1508, the backing plate 1504, and the tag body 1502 while allowing the tag body 1502 and the backing plate 1504 to move along the post 1508, for example.

As one example, a diameter of the holes within the tag body 1502 and the backing plate 1504 may be less than a diameter or other dimension of the end portion 1512 to provide a press or friction fit. The end portion 1512, the holes within the backing plate 1504 and the tag body 1502, or both may be configured to deform (e.g., be made from a deformable or non-rigid material) as the end portion 1512 of the post 1508 is pressed through the holes of the tag body 1502 and the backing plate 1504, for example.

The backing plate 1504 can slide along the post 1508 toward and away from the tag body 1502. A spring 1514 can provide a compressive force against the backing plate 1504 by forcing the backing plate 1504 toward the tag body 1502.

The spring 1514 can be compressed between the backing plate 1504 and an anchor plate 1516, for example. The anchor plate 1516 can extend from and orthogonally to the post 1508.

The spring 1514 can force the backing plate 1504 toward the tag body 1502 and can be stopped by a spacer 1518 between the backing plate 1504 and the tag body 1502. It is contemplated that the spacer 1518 can be integrally formed with the tag body 1502, the backing plate 1504, the post 1508, or a combination thereof.

The spacer 1518 can be designed, for example, to provide proper spacing between the tag body 1502 and the backing plate 1504 based on the type and location of the animal tissue 106 of FIG. 1 to be contacted. The spring 1514 can provide solid mechanical contact between the tag body 1502, the backing plate 1504 and the animal tissue 106 therebetween. The solid mechanical contact between the tag body 1502, the backing plate 1504, and the animal tissue 106 therebetween, can be important in providing consistent readings from the optical sensors 212.

It has been discovered that in some embodiments when the animal tissue 106 has sufficiently large blood vessels, such as with cattle, the tag 102 need not puncture through the animal tissue 106. Rather, effective readings can be achieved with firm pressure providing direct contact between the tag 102 and the animal tissue 106; for example, by way of friction fittings, magnets, springs, or a combination thereof.

The spacer 1518 can include the optical sensor 212 and the light sources 208. It will be appreciated that the optical sensor 212 positioned on the spacer 1518 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the spacer 1518.

For the purposes of this disclosure when the light sources 208 and the optical sensors 212 are both positioned on the same surface of the tag body 1502, the post 1508, the backing plate 1504, or the spacer 1518, the light sources 208 and the optical sensors 212 can be understood to be positioned on a single surface. Illustratively here, the optical sensor 212 and the light sources 208 are shown positioned on a single surface of the spacer 1518.

The light sources 208 can include multiple sources of light for various measurements. For example, the light sources 208 can include a red to infrared source 1520. The red to infrared source 1520 can be utilized to determine or measure peripheral blood oxygen saturation based on the absorption characteristics of the red to infrared light emitted from the red to infrared source 1520.

The light sources 208 can further include an ultraviolet source 1522, for example. The ultraviolet source 1522 can be utilized to determine the concentrations of blood urea based on the absorption characteristics of the ultraviolet light emitted from the ultraviolet source 1522.

Figure 16:
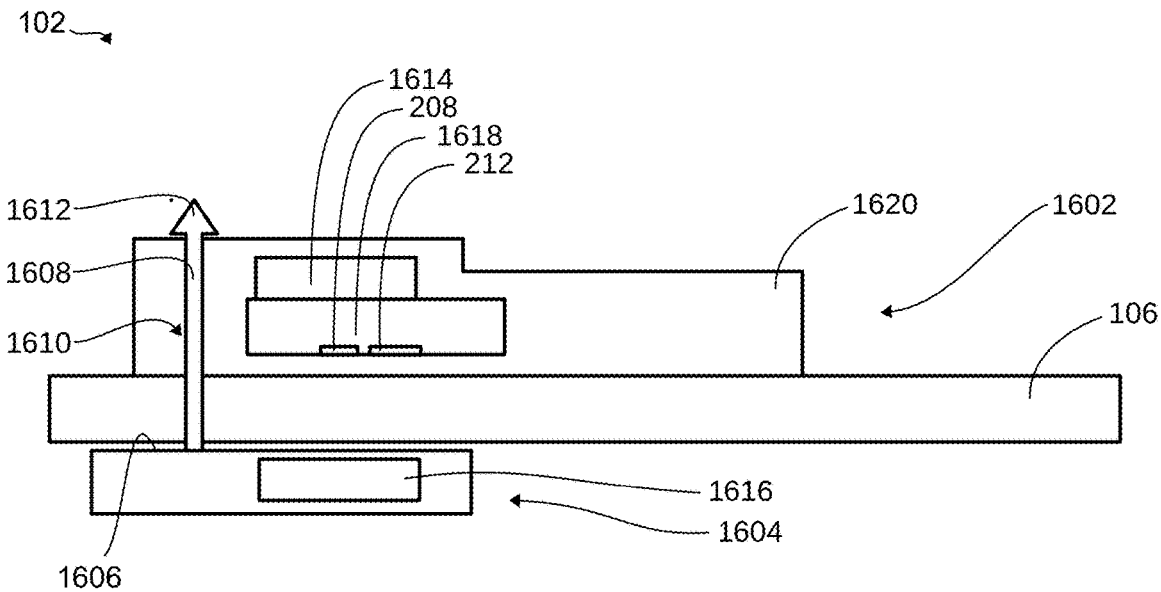
FIG. 16 is a cross-sectional view of the tag of FIG. 1 in a twelfth embodiment.

Referring now to FIG. 16, therein is shown a cross-sectional view of the tag 102 of FIG. 1 in a twelfth embodiment. The tag 102 can include two components including a tag body 1602 and a backing plate 1604.

The backing plate 1604 can include a posted side 1606 having a single post 1608 extending therefrom while the tag body 1602 can include a hole 1610 therethrough. The post 1608 can include an end portion 1612. The end portion 1612 can be a conical point configured to pass through the animal tissue 106 and through the hole 1610 of the tag body 1602.

Solid mechanical contact between the tag body 1602, the backing plate 1604 and the animal tissue 106 therebetween, can be ensured by the interference fit of the post 1608 extending through and contacting the hole 1610. Solid mechanical contact between the tag body 1602, the backing plate 1604 and the animal tissue 106 therebetween, can further be ensured by the physical contact between the hole 1610 and the end portion 1612 when inserted through the hole 1610.

As one example, a diameter of the hole 1610 may be less than a diameter or other dimension of the end portion 1612 to provide a press or friction fit. The end portion 1612, the hole 1610, or both may be configured to deform (e.g., be made from a deformable or non-rigid material) as the end portion 1612 is pressed through the holes 1610, for example.

The backing plate 1604 and the tag body 1602 are further depicted to include magnets. The magnets can include a tag body magnet 1614 and a backing plate magnet 1616. The tag body magnet 1614 and the backing plate magnet 1616 can be positioned on the backing plate 1604 and the tag body 1602 to ensure that only one rotational position of the backing plate 1604 and tag body 1602 will result in alignment between the tag body magnet 1614 and the backing plate magnet 1616 on the tag body 1602.

The optical sensor 212 and the light source 208 can be formed on or affixed to a printed circuit board 1618. The printed circuit board 1618, the optical sensor 212, and the light source 208 can be encapsulated in an optically clear encapsulation 1620.

The optically clear encapsulation 1620 can be similar in form and material as the first sealant 1002 of FIG. 10 and the second sealant 1008 of FIG. 10. It is contemplated that the optically clear encapsulation 1620 can be transparent in the light frequency range emitted by the light source 208 and received or detected by the optical sensor 212.

Other contemplated embodiments can include filters, embedded within or laminated over, the optically clear encapsulation 1620 to filter out unwanted light frequency ranges. It is contemplated that the optically clear encapsulation 1620 should have an index of refraction similar to or correlated to an index of refraction for the animal tissue 106, which can be between 1.3 and 1.4.

As will be appreciated the light emitted from the light source 208 will travel through the magnetic field between the tag body magnet 1614 and the backing plate magnet 1616. That is, an optical path of the light used by the light source 208 and the optical sensor 212 is sandwiched within and is in-line with the magnetic field produced by the tag body magnet 1614 and the backing plate magnet 1616.

The light from the light source 208, therefore, can be emitted, travel through the optically clear encapsulation 1620, and into the animal tissue 106. The light from the light source 208 will then be reflected back through the animal tissue 106, through the optically clear encapsulation 1620, and into the optical sensor 212. It will be appreciated that the light can travel without passing through the magnetic fields of the tag body magnet 1614 or the backing plate magnet 1616.

The tag body magnet 1614 and the backing plate magnet 1616 can produce a solid mechanical contact between the tag body 1602, the backing plate 1604 and the animal tissue 106 therebetween. This solid mechanical contact can be ensured by the pull between the tag body magnet 1614 on the backing plate magnet 1616. The solid mechanical contact between the tag body 1602, the backing plate 1604, and the animal tissue 106 therebetween, can be important in providing consistent readings from the optical sensors 212.

The tag body magnet 1614 and the backing plate magnet 1616 also take weight off the post 1608 preventing the animal tissue 106 from sagging from the weight of the tag 102. It is contemplated that the tag body magnet 1614, the backing plate magnet 1616, the post 1608 can be used together or in combination with an additional post in order to get the proper optical-mechanical coupling.

The optical sensor 212 positioned on the printed circuit board 1618 within the optically clear encapsulation 1620 of the tag body 1602 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the tag body 1602.

For the purposes of this disclosure when the light sources 208 and the optical sensors 212 are both positioned within and along the same surface of the tag body 1602. The light sources 208 and the optical sensors 212 can be understood to be positioned on, within, or along a single surface.

Figure 17:
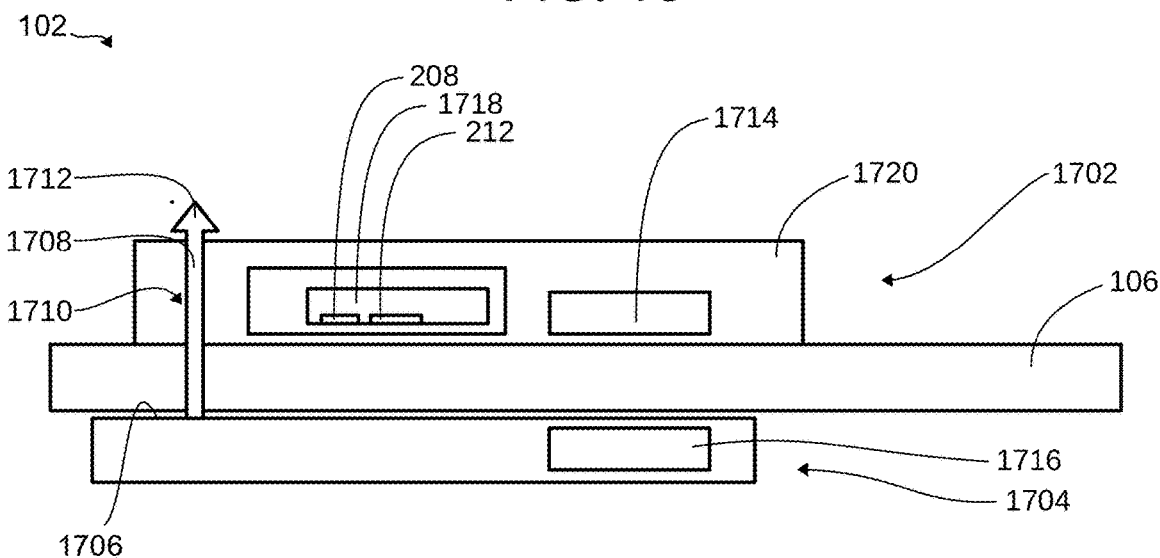
FIG. 17 is a cross-sectional view of the tag of FIG. 1 in a thirteenth embodiment.

Referring now to FIG. 17, therein is shown a cross-sectional view of the tag 102 of FIG. 1 in a thirteenth embodiment. The tag 102 can include two components including a tag body 1702 and a backing plate 1704.

The backing plate 1704 can include a posted side 1706 having a single post 1708 extending therefrom while the tag body 1702 can include a hole 1710 therethrough. The post 1708 can include an end portion 1712. The end portion 1712 can be a conical point configured to pass through the animal tissue 106 and through the hole 1710 of the tag body 1702.

Solid mechanical contact between the tag body 1702, the backing plate 1704 and the animal tissue 106 therebetween, can be ensured by the interference fit of the post 1708 extending through and contacting the hole 1710. Solid mechanical contact between the tag body 1702, the backing plate 1704 and the animal tissue 106 therebetween, can further be ensured by the physical contact between the hole 1710 and the end portion 1712 when inserted through the hole 1710.

As one example, a diameter of the hole 1710 may be less than a diameter or other dimension of the end portion 1712 to provide a press or friction fit. The end portion 1712, the hole 1710, or both may be configured to deform (e.g., be made from a deformable or non-rigid material) as the end portion 1712 is pressed through the holes 1710, for example.

The backing plate 1704 and the tag body 1702 are further depicted to include magnets. The magnets can include a tag body magnet 1714 and a backing plate magnet 1716. The tag body magnet 1714 and the backing plate magnet 1716 can be positioned on the backing plate 1704 and the tag body 1702 to ensure that only one rotational position of the backing plate 1704 and tag body 1702 will result in alignment between the tag body magnet 1714 and the backing plate magnet 1716 on the tag body 1702.

The optical sensor 212 and the light source 208 can be formed on or affixed to a printed circuit board 1718. The printed circuit board 1718, the optical sensor 212, and the light source 208 can be encapsulated in an optically clear encapsulation 1720.

The optically clear encapsulation 1720 can be similar in form and material as the first sealant 1002 of FIG. 10 and the second sealant 1008 of FIG. 10. It is contemplated that the optically clear encapsulation 1720 can be transparent in the light frequency range emitted by the light source 208 and received or detected by the optical sensor 212.

Other contemplated embodiments can include filters, embedded within or laminated over, the optically clear encapsulation 1720 to filter out unwanted light frequency ranges. It is contemplated that the optically clear encapsulation 1720 should have an index of refraction similar to or correlated to an index of refraction for the animal tissue 106, which can be between 1.3 and 1.4.

As will be appreciated the light emitted from the light source 208 will travel beside and out of the plane of the magnetic field between the tag body magnet 1714 and the backing plate magnet 1716. That is, an optical path of the light used by the light source 208 and the optical sensor 212 is positioned outside of the magnetic field produced by the tag body magnet 1714 and the backing plate magnet 1716.

The light from the light source 208, therefore, can be emitted, travel through the optically clear encapsulation 1720, and into the animal tissue 106. The light from the light source 208 will then be reflected back through the animal tissue 106, through the optically clear encapsulation 1720, and into the optical sensor 212. It will be appreciated that the light can travel without passing through the magnetic fields of the tag body magnet 1714 or the backing plate magnet 1716.

The tag body magnet 1714 and the backing plate magnet 1716 can produce a solid mechanical contact between the tag body 1702, the backing plate 1704 and the animal tissue 106 therebetween. This solid mechanical contact can be ensured by the pull between the tag body magnet 1714 on the backing plate magnet 1716. The solid mechanical contact between the tag body 1702, the backing plate 1704, and the animal tissue 106 therebetween, can be important in providing consistent readings from the optical sensors 212.

The tag body magnet 1714 and the backing plate magnet 1716 also take weight off the post 1708 preventing the animal tissue 106 from sagging from the weight of the tag 102. It is contemplated that the tag body magnet 1714, the backing plate magnet 1716, the post 1708 can be used together or in combination with an additional post in order to get the proper optical-mechanical coupling.

The optical sensor 212 positioned on the printed circuit board 1718 within the optically clear encapsulation 1720 of the tag body 1702 can provide a reflective signal (e.g., light emitted by the light source 208 is reflected and/or scattered by structure within the animal tissue 106) in that a portion of the light emitted by the light sources 208 reflects from within the animal tissue 106 and is received by (e.g., is incident on) the optical sensor 212 positioned on the tag body 1702.

For the purposes of this disclosure when the light sources 208 and the optical sensors 212 are both positioned within and along the same surface of the tag body 1702. The light sources 208 and the optical sensors 212 can be understood to be positioned on, within, or along a single surface.

Figure 18:
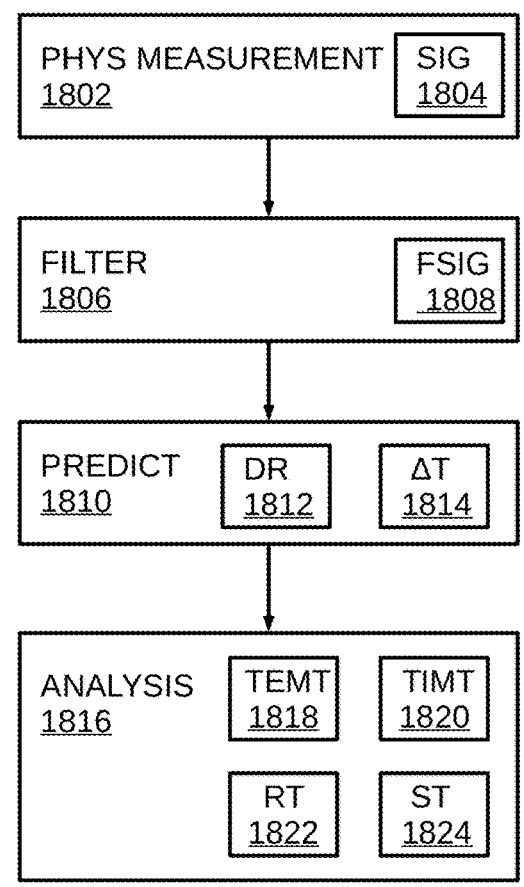
FIG. 18 is a first control flow for the determination system of FIG. 1.

Referring now to FIG. 18, therein is shown a first control flow 1800 for the determination system 100 of FIG. 1. The determination system 100 can begin by initiating a physiological measurement step 1802.

The tag 102 of FIG. 1 can execute the physiological measurement step 1802 utilizing the light source 208 of FIG. 2 and the optical sensor 212 of FIG. 2 every two minutes to thirty minutes. The optical sensor 212 can generate a signal 1804 based on detecting light that is not absorbed, by the animal tissue 106 of FIG. 1 or the oxygenated and deoxygenated blood therein, after being emitted by the light source 208.

The signal 1804 can include one or more physiological components, which can be measured, including but not limited to heart rate, heart rate variability, respiration rate, respiration rate variability, saturation of peripheral oxygen (SpO2), temperature, blood urea, and physiological components associated with the sympathetic nervous system to be computed. For example, the signal 1804 can include a respiratory component enabling a respiratory rate, respiratory variability to be calculated. The signal 1804 can further have a heart rate component enabling a heart rate and heart rate variability to be calculated.

The signal 1804 can also have an SpO2 component enabling the SpO2 to be calculated. For example, the absorption of light can be greater when the amount of blood in the animal tissue 106 increases as part of a heartbeat. Further, the absorption rate can change based on a longer breathing cycle changing the amount of oxygen carried by the blood within the animal tissue 106.

In some contemplated embodiments, the signal 1804 can also include peripheral temperature measurements from the temperature sensor 814 of FIG. 8 and/or inertial sensors monitoring the posture and activity level of the animal. Once the signal 1804 is obtained, the determination system 100 can execute a filter step 1806.

The filter step 1806 can filter out measurement artifacts including, motion artifacts, obscurement artifacts, and environmental artifacts such as ambient light. The signal 1804 can be filtered by executing the filter step 1806 on the processors 222 of FIG. 2 contained within the tag 102 or can be filtered by executing the filter step 1806 on the computation module 242 of FIG. 2 of the network 104 of FIG. 1.

The result of the filter step 1806 can be a filtered signal 1808 having a large reduction in measurement artifacts. It is contemplated that the filter step 1806 can also include the respiratory rate, respiratory variability, heart rate, heart rate variability, SpO2, and blood urea concentration as isolated and individual signals for later use.

The individual signals of the respiratory rate, respiratory variability, heart rate, heart rate variability, SpO2, and blood urea concentration within the filtered signal 1808 can be determined during the filter step 1806, the physiological measurement step 1802, or alternatively, within a separate and dedicated step. Once the filtered signal 1808 is obtained within the filter step 1806, the determination system 100 can initiate a prediction step 1810.

The prediction step 1810 can implement a regression analysis to estimate the change in core temperature of the livestock (e.g., a change in core body temperature of an animal or a mammal). That is, the change in heart rate and change in SpO2 can be used to determine a change in core temperature.

Illustratively in cattle, core temperature is positively correlated to heart rate in that an increase in ten beats per minute would correlate to one degree rise in core temperature. Similarly, in cattle, core temperature is negatively correlated to SpO2 in that a drop of five percent from a baseline SpO2 would correlate to a three degree increase in core temperature.

In one contemplated implementation, the prediction step 1810 could rely on an equation such as: $\Delta temp = ax_1 + bx_2$. Where "a" can indicate the weight given to a negative change in SpO2 represented by $x_1$, and "b" can indicate the weight given to a positive change in heart rate represented by $x_2$. It is contemplated that the change in SpO2 can be given a larger weight in the determination of $\Delta temp$ than the change in heart rate.

The prediction step 1810 can further normalize the change in temperature, detected based on the heart rate and the SpO2, with a diurnal rhythm 1812. That is, changes in core temperature are normal and expected based on wake-sleep cycles. The change in temperature estimated based on the heart rate and SpO2 can be understood in relation to the expected diurnal temperature changes.

The prediction step 1810 can therefore output an estimated change in core temperature 1814 that is normalized to the diurnal rhythm 1812 meaning the estimated change in core temperature 1814 can be the estimated core temperature change above or below what is expected from the diurnal rhythm 1812. The estimated change in core temperature 1814 can further be qualified by obtaining information about an animal's movement and posture based on the readings of an accelerometer or an IMU, which can be used to distinguish between changes caused by movement and changes caused by infection.

The estimated change in core temperature 1814 can be determined by executing the prediction step 1810 on the computation module 242 of the network 104. Once the prediction step 1810 has determined the estimated change in core temperature 1814, the determination system 100 can initiate an analysis step 1816.

The analysis step 1816 can implement thresholds to determine whether a condition of concern exists. It is contemplated the analysis step 1816 can include a temperature threshold 1818, a time threshold 1820, a respiratory threshold 1822, and stress thresholds 1824.

The temperature threshold 1818 can be met if the estimated change in core temperature 1814 is determined to meet or exceed the temperature threshold 1818. For example, if the temperature threshold 1818 is four degrees Celsius and the estimated change in core temperature 1814 is four degrees Celsius, the temperature threshold 1818 would be met.

Alternatively, a temperature threshold could be met if temperature increases faster pre-determined rate. This could, for example, be considered the temperature threshold 1818 based on a derivative.

The time threshold 1820 can be a secondary threshold used only when the temperature threshold 1818 is met. For example, if the temperature threshold 1818 is met and the time threshold 1820 is six hours, the time threshold 1820 would be met when the estimated change in core temperature 1814 is at or above the temperature threshold 1818 for six hours or more.

Alternatively, it is contemplated that the time threshold 1820 could be employed when, for example, a calculated temperature rises above a temperature threshold 1818 for a time exceeding the time threshold 1820. This could be exemplified by the temperature of a cow calculated above 39.5 degrees Celsius for more than two hours triggering an alarm. It is contemplated that when the temperature threshold 1818 and the time threshold 1820 are met, an alert condition for the tag 102 can be generated and the tag 102 can illuminate the signal LED within the user interface 214 of FIG. 2.

The thresholds could further be targeted to a specific disease or condition such as bovine respiratory disease, bovine anemia, and Foot and Mouth Disease. For example, the respiratory threshold 1822 can be triggered when the respiratory variability reaches or exceeds the respiratory threshold 1822. When the respiratory threshold 1822 is met, the tag 102 could also be instructed to illuminate the signal LED within the user interface 214 of the tag 102.

Yet other thresholds could be implemented to detect conditions such as stress. For example, the stress thresholds 1824 can be met when heart rate and respiratory rate increase above the stress thresholds 1824 causing an alarm state.

It is contemplated that when the analysis step 1816 determines that a threshold is met and a condition exists, the alarm and the triggering data can be displayed on the display 112 of FIG. 1 for proper treatment or handling of the animal.

Figure 19:
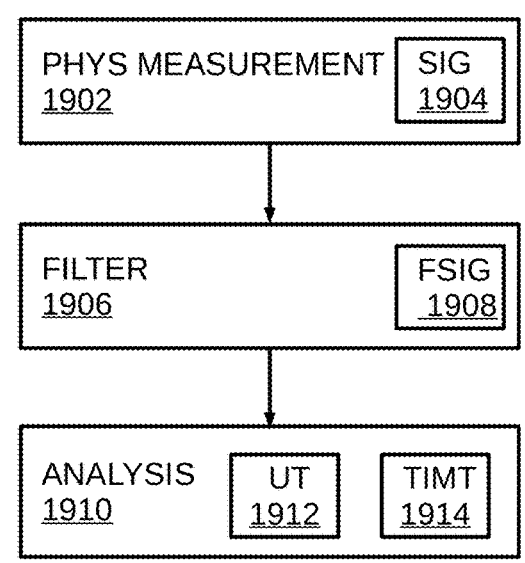
FIG. 19 is a second control flow for the determination system of FIG. 1.

Referring now to FIG. 19, therein is shown a second control flow 1900 for the determination system 100 of FIG. 1. The determination system 100 can begin by initiating a physiological measurement step 1902.

The tag 102 of FIG. 1 can execute the physiological measurement step 1902 utilizing the ultraviolet source 922 of FIG. 9, for example, and the optical sensor 212 of FIG. 2 every two minutes to thirty minutes. The optical sensor 212 can generate a signal 1904 based on detecting light that is not absorbed, by the animal tissue 106 of FIG. 1 or the blood urea therein, after being emitted by the ultraviolet source 922.

The signal 1904 can include one or more physiological components including the concentration of blood urea. Once the signal 1904 is obtained, the determination system 100 can execute a filter step 1906.

The filter step 1906 can filter out measurement artifacts including, motion artifacts, obscurement artifacts, and environmental artifacts such as ambient light. The signal 1904 can be filtered by executing the filter step 1906 on the processors 222 of FIG. 2 contained within the tag 102 or can be filtered by executing the filter step 1906 on the computation module 242 of FIG. 2 of the network 104 of FIG. 1.

The result of the filter step 1906 can be a filtered signal 1908 having a large reduction in measurement artifacts. Once the filtered signal 1908 is obtained within the filter step 1906, the determination system 100 can initiate an analysis step 1910.

The analysis step 1910 can implement thresholds to determine whether a condition of concern exists. It is contemplated the analysis step 1910 can include a urea threshold 1912, and a time threshold 1914.

The urea threshold 1912 can be met if the estimated concentration of blood urea is determined to meet or exceed the urea threshold 1912. Alternatively, the urea threshold 1912 could be met if blood urea concentrations increase faster pre-determined rate, for example.

The time threshold 1914 can be a secondary threshold used only when the urea threshold 1912 is met. For example, if the urea threshold 1912 is met and the time threshold 1914 is six hours, the time threshold 1914 would be met when the concentration of blood urea is at or above the urea threshold 1912 for six hours or more.

Alternatively, it is contemplated that the time threshold 1914 could be employed when the concentration of blood urea rises above the urea threshold 1912 during certain hours of the day, for example, when the animal is expected to be sleeping and blood urea concentrations expected to be low, for example. It is contemplated that when the urea threshold 1912 and the time threshold 1914 are met, an alert condition for the tag 102 can be generated and the tag 102 can illuminate the signal LED within the user interface 214 of FIG. 2.

It is contemplated that when the analysis step 1910 determines that a threshold is met and a condition exists, the alarm and the triggering data can be displayed on the display 112 of FIG. 1 for proper treatment or handling of the animal.

Figure 20:
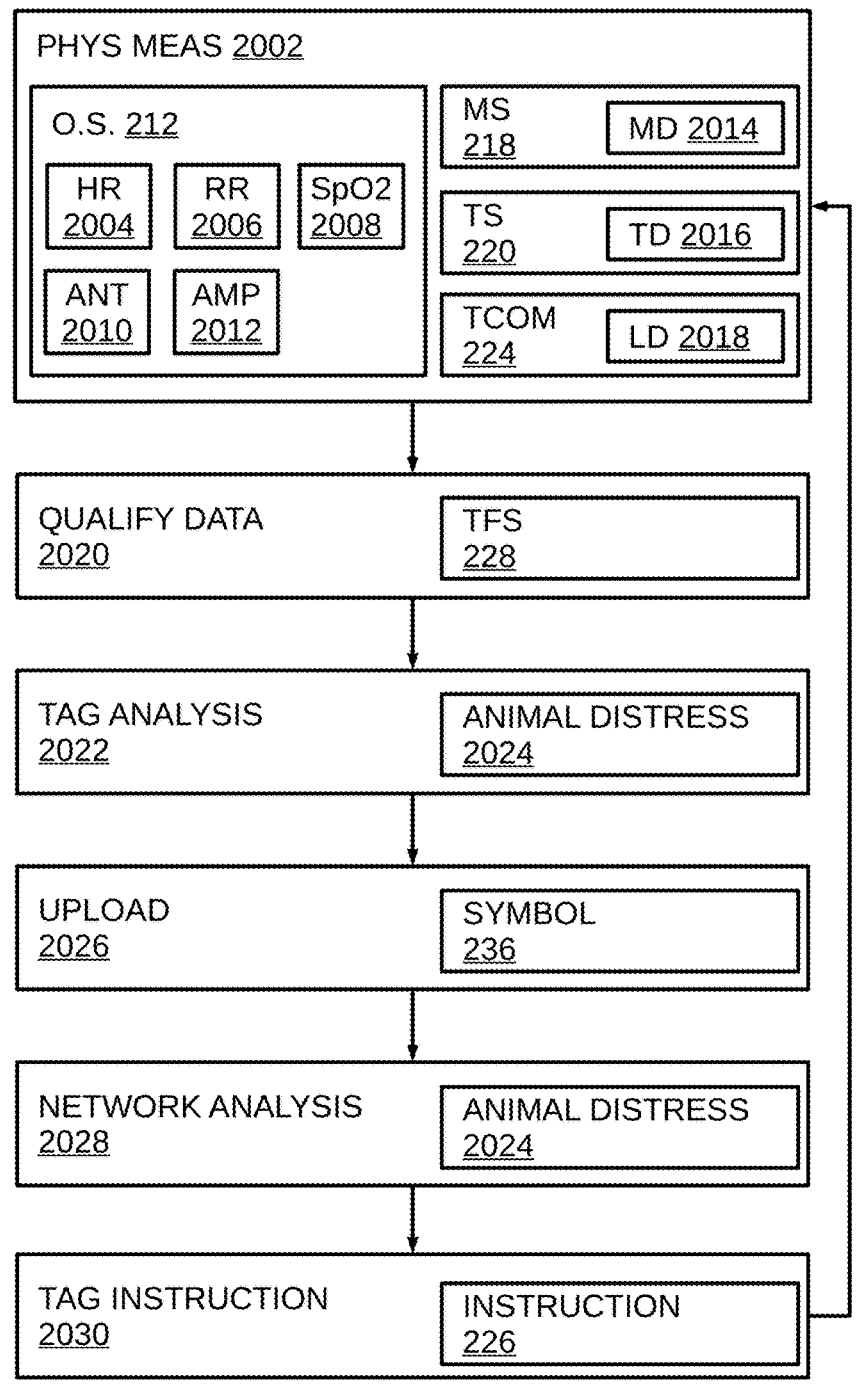
FIG. 20 is a third control flow for the determination system of FIG. 1.

Referring now to FIG. 20, therein is shown a third control flow 2000 for the determination system 100 of FIG. 1. The determination system 100 can begin by initiating a physiological measurement step 2002.

The tag 102 of FIG. 1 can execute the physiological measurement step 2002 utilizing the light source 208 of FIG. 2 and the optical sensor 212 of FIG. 2 every two minutes to thirty minutes, for example.

The optical sensor 212 can generate an optical signal based on detecting light that is not absorbed, by the animal tissue 106 of FIG. 1 or the oxygenated and deoxygenated blood therein, after being emitted by the light source 208.

The optical signal can include one or more physiological components, which can be measured, including but not limited to heart rate 2004, heart rate variability, respiration rate 2006, respiration rate variability, saturation of peripheral oxygen (SpO2) 2008, animal temperature 2010, blood urea, arterial mean pressure 2012, and physiological components associated with the sympathetic nervous system to be computed. For example, the optical signal can include a respiratory component enabling a respiratory rate, respiratory variability to be calculated. The optical signal can further have a heart rate component enabling a heart rate and heart rate variability to be calculated.

The optical signal can also have an SpO2 component enabling the SpO2 to be calculated. For example, the absorption of light can be greater when the amount of blood in the animal tissue 106 increases as part of a heartbeat. Further, the absorption rate can change based on a longer breathing cycle changing the amount of oxygen carried by the blood within the animal tissue 106.

The physiological measurement step 2002 can further include readings and measurements from the motion sensor 218, the thermal sensor 220, and the tag communications module 224 in addition to or in place of the measurements taken from the optical sensor 212. Illustratively, the motion sensor 218 can provide motion data 2014, the thermal sensor 220 can provide temperature data 2016, and the tag communications module 224 can provide location data 2018.

The motion data 2014 can be an acceleration measurement and the temperature data 2016 can be the ambient temperature around the tag 102. The location data 2018 can be a triangulation of the tag 102, for example, based on an RSSI triangulation, or can be a reading of the network 104 antennae 108 with the strongest signals.

It is contemplated that the heart rate 2004, the respiration rate 2006, the SpO2 2008, the animal temperature 2010, the arterial mean pressure 2012, the motion data 2014, the temperature data 2016, and the location data 2018 can be stored as histories within the computer readable media 216 of FIG. 2 of the tag 102. It is contemplated that the histories could include multiple days' worth of data, for example, from three to five days' worth of historical data.

It has been discovered that storing the heart rate 2004, the respiration rate 2006, the SpO2 2008, the animal temperature 2010, the arterial mean pressure 2012, the motion data 2014, the temperature data 2016, the location data 2018, or a combination thereof as histories within the computer readable media 216 of the tag 102 can reduce the amount of computing resources and infrastructure required to transfer the animals because the animal's data can travel with the animal as the histories stored in the computer readable media 216.

It has been discovered that storing the heart rate 2004, the respiration rate 2006, the SpO2 2008, the animal temperature 2010, the arterial mean pressure 2012, the motion data 2014, the temperature data 2016, the location data 2018, or a combination thereof as histories within the computer readable media 216 of the tag 102 can enable more effective processing of the data, for example, by enabling the longitudinal statistical model 230 to be applied over time to the data.

Once the physiological measurement step 2002 has been complete, the determination system 100 can execute a qualify data step 2020. During the qualify data step 2020, the determination system 100 can qualify the measurement features 229 of FIG. 2 from the optical sensor 212 prior to expending computer resources to extract and identify the data of the measurement features 229 representing the physiological components from the optical signal or prior to further statistical processing of the data from the optical sensor 212.

For example, the determination system 100 can implement the data rules 234 of FIG. 2 in order to qualify the measurement features 229 of the data from the optical sensor 212. For example, the tag 102 can disregard or delete the data from the optical sensor 212 if the motion data 2014 indicates motion or a change in motion, which would correlate with a higher likelihood of motion artifacts in the optical signal of the optical sensor 212.

As a further example, the tag 102 can disregard or delete the data from the optical sensor 212 if the location data 2018 indicates the tag 102 is in a location, such as near or within a feed trough, which would correlate with a statistically higher heart rate 2004 than baseline.

As yet a further example, the tag 102 can disregard or delete the data from the optical sensor 212 if the temperature data 2016 indicates the ambient temperature around the tag 102 is above or below a preferred temperature envelope. Ambient temperature has been shown to correlate with blood profusion in animal tissue and thus has a direct impact on the quality of the optical signal of the optical sensor 212, thus readings taken by the optical sensor 212 at temperatures above or below a temperature envelope can suffer from quality degradation and can be disregarded or deleted.

As yet a further example, the tag 102 data including the measurement features 229 can be qualified by the time the measurement was taken, which can remove or avoid effects of circadian rhythm and the effects of regular feeding and drinking.

It is further contemplated that each type of measurement feature 229, including the heart rate 2004, the respiration rate 2006, the SpO2 2008, the animal temperature 2010, the arterial mean pressure 2012, the motion data 2014, the temperature data 2016, and the location data 2018 can be qualified with the history of the same type of data from a specific animal longitudinally using the longitudinal statistical model 230 of FIG. 2 or from aggregated statistic of a herd using the aggregated statistical model 232 of FIG. 2.

The qualified data or the measurement features 229 from the qualify data step 2020 can be stored in the computer readable media 216 as the tag feature sets 228. Multiple tag feature sets 228 can be stored to provide a historical record on the computer readable media 216 of the tag 102 for each individual animal.

The determination system 100 can further execute a tag analysis step 2022. The tag analysis step 2022 can utilize the longitudinal statistical model 230 and the aggregated statistical model 232 to detect multiple patterns of animal distress 2024 including: BRD, bloat, heat stress, other illnesses, stress, and calving, for example.

In one illustrative example, inflammation including BRD can be detected with a statistically significant drop in the SpO2 2008, and an increase in the core temperature, which can be derived from the heart rate 2004 and the SpO2 2008. Detection of inflammation especially BRD can be important to prevent further infection within a herd and to prevent the death of the animal.

In another illustrative example, bloat can be detected with a statistically significant and dangerous drop in the SpO2 2008 alone or in combination with a spike in the heart rate 2004 detected. A dangerous drop can, for example, be a drop in the SpO2 2008 below 90% saturation. Detection of bloat can be important to prevent death of the animal.

In another illustrative example, heat stress can be detected with a statistically significant rapid respiratory cycle impacting both the heart rate 2004 and the SpO2 2008, elevated core temperature derived from the SpO2 2008 and the heart rate 2004, and elevated temperature data 2016. A rapid respiratory cycle can be a respiratory cycle faster than an average respiratory cycle of a similar healthy animal moving at a walking pace. Detection of heat stress can be important to prevent death of the animal and decreased feedlot performance in terms of weight gain.

In another illustrative example, other illnesses can be detected with a statistically significant reduction in motion data 2014 indicating lethargy or depression along with a rise in the core temperature derived from the heart rate 2004 and the SpO2 2008. Detection of other illnesses can be important to prevent death of the animal, infection of the herd, and decreased feedlot performance in terms of weight gain.

In another illustrative example, stress can be detected with a statistically significant increase in the variability of the heart rate 2004 together with the motion data 2014. Detection of stress can be important prevent decreased feedlot performance in terms of weight gain.

In another illustrative example, calving can be detected with a statistically significant SpO2 2008 cycles, heart rate 2004 cycles, and motion data 2014 patterns. Detection of stress can be important in providing timely assistance and event management.

During the tag analysis step 2022 it is contemplated that the individual contribution of the heart rate 2004, the respiration rate 2006, the SpO2 2008, the animal temperature 2010, the arterial mean pressure 2012, the motion data 2014, the temperature data 2016, and the location data 2018 to the determination and detection of the animal distress 2024 can be qualified by a set of weighting functions based on longitudinal information from an animal, aggregated information from a herd of animal, age, sex, bred of the animal and by other objective or subjective determined methods discovered from livestock farmer's experience and/or machine learning methods.

The determination system 100 can perform an upload step 2026 during which the symbols 236 can be uploaded from the tag 102 to the network 104. It is contemplated that the symbols 236 can include an encoded or compressed representation of the tag feature sets 228 determined during the qualify data step 2020 and the animal distress 2024 determined during the tag analysis step 2022.

The determination system 100 can further initiate a network analysis step 2028. During the network analysis step 2028, the longitudinal statistical model 230 and the aggregated statistical model 232 can be used at the network 104 level to detect multiple patterns of the animal distress 2024 as discussed above with regard to the tag analysis step 2022. Further, during the network analysis step 2028, the measurement features 229 can be qualified at the network 104 level in a manner described in qualify data step 2020.

The network analysis step 2028 can be executed in place of the tag analysis step 2022 or in addition to the tag analysis step 2022 when additional information is available at the network 104 level. For example, the network 104 may have access to longitudinal information from an animal, aggregated information from a herd of animal, the age, the sex, the bred of the animal and other objective or subjective information not detected or accessible to the tag 102.

For ease of illustration, the qualify data step 2020 and the tag analysis step 2022 have been described as being performed on the tag 102 utilizing the components and hardware of the tag 102, however it is contemplated that the determination system 100 could also execute these steps at the network 104 level and employ network 104 resources rather than the tag 102 for partitioning the computational load of the qualify data step 2020, the tag analysis step 2022, the upload step 2026 or a combination thereof.

Specifically, the partitioning of computational resources between the tag 102 and the network 104 can be variable and can be determined by factors of the use cases for each individual tag 102. For example, when RF resources for upload are plentiful in term of power and access to the network 104, the tag 102 could upload all the raw data, including the measurement features 229, collected by the optical sensor 212, the motion sensor 218, the thermal sensor 220, and the tag communications module 224 prior to the qualify data step 2020. It is contemplated that this scenario would be the case with the lowest computational resources required by the tag 102 and the highest transmission resources required, in terms of RF power, by the tag 102.

As an alternative example, the tag 102 could upload raw data, together with the measurement features 229, collected by the optical sensor 212, the motion sensor 218, the thermal sensor 220, and the tag communications module 224 prior to the qualify data step 2020 after applying some data quality analysis, such as those described with regard to the qualify data step 2020.

As another alternative example, the tag 102 could upload the tag feature sets 228 to the network 104 after the measurement features 229 from the optical sensor 212, the motion sensor 218, the thermal sensor 220, and the tag communications module 224 have been qualified during the qualify data step 2020.

Yet further, it is contemplated that some or all of the analysis to determine animal distress 2024 can be performed on the tag 102 and uploaded to the network 104 or alternatively, some or all of the analysis to determine animal distress 2024 can be performed at the network 104 level. As will be appreciated, the more processing of the raw data performed by the tag 102 the more computational resources will be required of the tag 102, while the less processing of the raw data performed by the tag 102 the more RF resources will be required by the tag 102.

The determination system 100 can next execute a tag instruction step 2030. During the tag instruction step 2030, the network 104 can generate and transmit the instruction 226 to the tag 102.

The instruction 226 can include a selection or identification of which data rules 234 the tag 102 should apply to qualify the measurement features 229 from the optical sensor 212, the motion sensor 218, the thermal sensor 220, and the tag communications module 224. The instruction 226 could further include an identification or request for which types of the heart rate 2004, the respiration rate 2006, the SpO2 2008, the animal temperature 2010, the arterial mean pressure 2012, the motion data 2014, the temperature data 2016, and the location data 2018 is to be included in the tag feature sets 228 and ultimately transmitted to the network 104 via the symbols 236.

The instruction 226 could further define how much, if any, analysis is to be performed by the tag 102 during the tag analysis step 2022 and how much analysis should be left for the network 104 during the network analysis step 2028. It is contemplated that the instruction 226 could change over time based on external factors such as the age of the animal, the amount of infrastructure supporting the tags 102, or specific concerns such as bloat causing diets, stress inducing transfers, and herd infections.

The instruction 226 can further include instructions for the operation and control of the optical sensor 212, the motion sensor 218, the thermal sensor 220, and the tag communications module 224. That is, the sampling rate, sampling duration, and sampling intensity can be modified or controlled by the network 104 by way of the instruction 226.

For example, the sampling rate could be set by the instruction 226 based on a fixed rate or rate patterns incorporating the circadian rhythm and feeding rhythms. Sampling could also be triggered by remote command from the network 104 within the instruction 226. The sampling command could be a command for a low, moderate, or high sampling rate based on the selection by an expert.

The sampling rate could be increased based on an increased risk of animal distress 2024 as determined by the longitudinal statistical model 230, the aggregated statistical model 232, or by a human assessment. The sampling rate could be decreased based on a decreased risk of animal distress 2024 as determined by the longitudinal statistical model 230, the aggregated statistical model 232, or by a human assessment.

Increased risk of animal distress 2024 can include animal transfers between different feed lots, detecting animal distress 2024 in other animals within the herd, a change in diet increasing the risk of bloat, detecting the temperature data 2016 outside of a normal envelope, or a combination thereof. Decreased risk of animal distress 2024 can include the animal spending multiple days acclimating to a feed lot. It is contemplated that other factors can be used to determine the risk of animal distress including the genetics of the animal, the age of the animal, the sex of the animal, or a combination thereof.

The sampling rate, for example, could be increased in order to bias away from false positives when comparing the heart rate 2004, the respiration rate 2006, the SpO2 2008, the animal temperature 2010, the arterial mean pressure 2012, the motion data 2014, the temperature data 2016, and the location data 2018 with historical measurements for each of the data types.

Further, the sampling rate could be controlled or modified by the instruction 226 based on the available power of the tag 102. For example, when the tag 102 is above an upper threshold of power the tag 102 may perform more of the physiological measurement step 2002, the qualify data step 2020, and the tag analysis step 2022, however, if the network 104 detects that the tag 102 has fallen below a lower threshold of power the amount of the physiological measurement step 2002, the qualify data step 2020, and the tag analysis step 2022 can be decreased to save power on the tag 102.

It is further contemplated that when the animal distress 2024 is detected, the network 104 can send instructions to the specific tag 102 measuring signals indicating the animal distress 2024 to activate the user interface 214 of FIG. 2. The activation of the user interface 214 can include flashing or lighting an LED, producing an audible alarm, or a combination thereof.

For ease of description, the upload step 2026 is shown and described as following the tag analysis step 2022, however it is contemplated that the tag 102 could perform the physiological measurement step 2002, the qualify data step 2020, and the tag analysis step 2022 multiple times prior to performing the upload step 2026 since the tag feature sets 228 are stored as longitudinal data within the computer readable media 216 of the tag 102.

Figure 21:
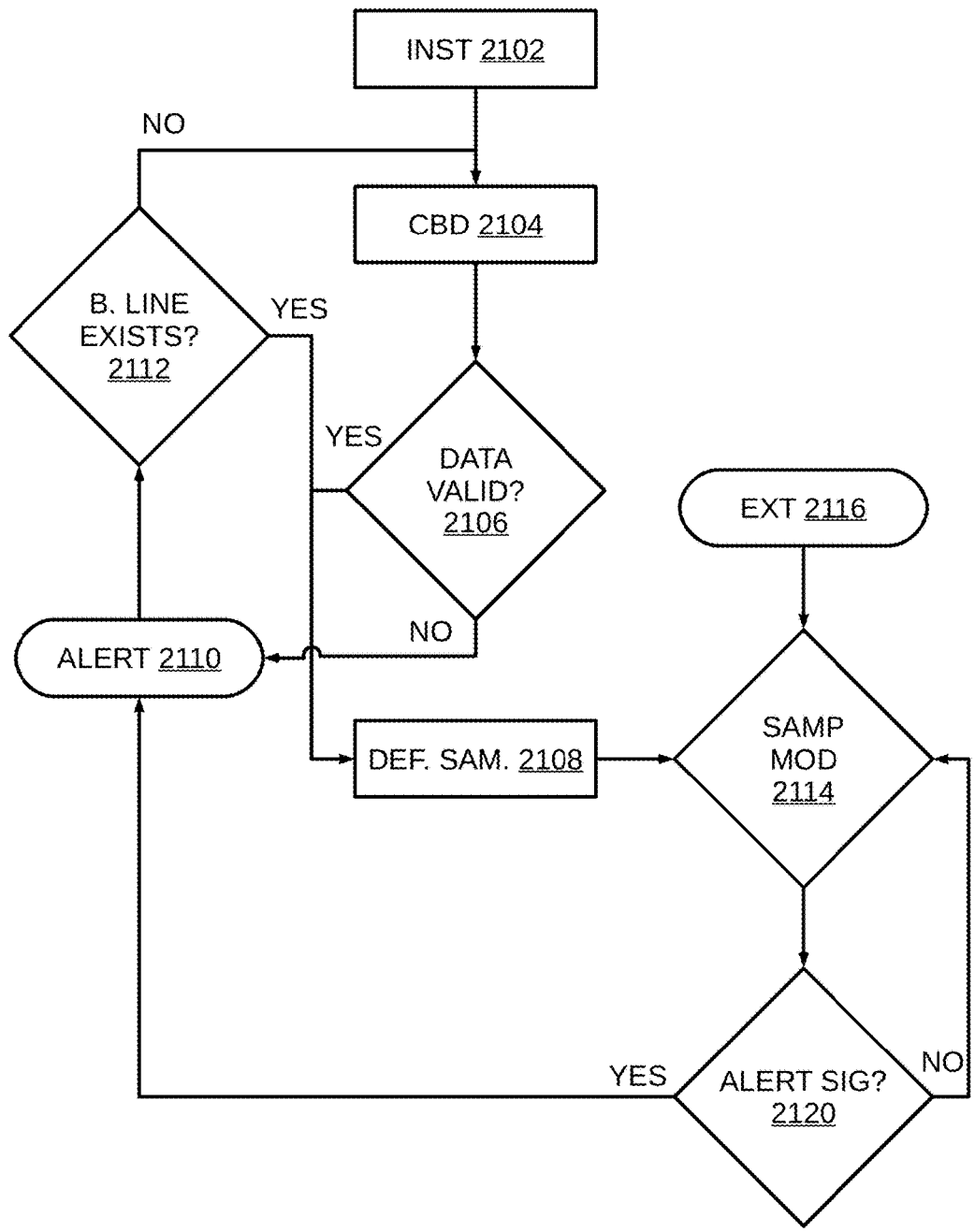
FIG. 21 is a fourth control flow for the determination system of FIG. 1.

Referring now to FIG. 21, therein is shown a fourth control flow 2100 for the determination system 100 of FIG. 1. The fourth control flow 2100 can implement the steps of the third control flow 2000 of FIG. 20 in addition to the steps described below with regard to FIG. 21.

The determination system 100 can first be implemented with an installation step 2102. During the installation step 2102, the tag 102 of FIG. 1 can be physically affixed to the animal tissue 106 of FIG. 1.

After the installation step 2102, the determination system 100 can implement a collect baseline data step 2104. During the collect baseline data step 2104 the measurement features 229 from the data of FIG. 20 can be collected including the heart rate 2004, the respiration rate 2006, the SpO2 2008, the animal temperature 2010, the arterial mean pressure 2012, the motion data 2014, the temperature data 2016, and the location data 2018. These measurement features 229 can be detected and stored in the computer readable media 216 of FIG. 2 of the tag 102 order to establish a baseline.

It is contemplated that the baseline can be a moving average for a time period, for example, the baseline could be a three day moving average for the heart rate 2004, the respiration rate 2006, the SpO2 2008, the animal temperature 2010, the arterial mean pressure 2012, the motion data 2014, the temperature data 2016, and the location data 2018.

The determination system 100 can initiate a baseline validity decision step 2106. The baseline validity decision step 2106 can analyze the data collected during the collect baseline data step 2104 to determine whether a statistically valid baseline for the measurement features 229, in the data from the tag 102, has been obtained.

If the measurement features 229 of the data obtained during the collect baseline data step 2104 is determined to be valid during the baseline validity decision step 2106, the determination system 100 can execute a default sampling step 2108. During the default sampling step 2108, the tag 102 can sample at a default frequency, duration, and configuration. Further, during the default sampling step 2108, the tag 102 can upload the tag feature sets 228 of FIG. 2 when upload is possible, which is based on environmental factors between the tag communications module 224 of FIG. 2 and the network communications module 244 of FIG. 2.

If the measurement features 229 of the data obtained during the collect baseline data step 2104 is determined to be invalid during the baseline validity decision step 2106, the determination system 100 can execute an alarm step 2110. The alarm step 2110 can prompt the network 104 of FIG. 1 to send the instruction 226 of FIG. 2 to the specific tag 102 measuring signals indicating the invalid baseline data to activate the user interface 214 of FIG. 2. The activation of the user interface 214 can include flashing or lighting an LED, producing an audible alarm, or a combination thereof.

After the alarm is activated during the alarm step 2110, the determination system 100 can initiate a baseline determination step 2112. During the baseline determination step 2112, the determination system 100 can determine whether a baseline for the heart rate 2004, the respiration rate 2006, the SpO2 2008, the animal temperature 2010, the arterial mean pressure 2012, the motion data 2014, the temperature data 2016, and the location data 2018 exists or still needs to be collected and established.

If the baseline determination step 2112 determines that the baseline does not exist for one or more of the heart rate 2004, the respiration rate 2006, the SpO2 2008, the animal temperature 2010, the arterial mean pressure 2012, the motion data 2014, the temperature data 2016, and the location data 2018, the collect baseline data step 2104 can be executed.

If the baseline determination step 2112 determines that the baseline does exist for the heart rate 2004, the respiration rate 2006, the SpO2 2008, the animal temperature 2010, the arterial mean pressure 2012, the motion data 2014, the temperature data 2016, and the location data 2018, the default sampling step 2108 can be executed.

Once the tag 102 has been instructed to sample at a default frequency, duration, and configuration during the default sampling step 2108, the determination system 100 can execute a sampling modification decision step 2114. The sampling modification decision step 2114 can be based on external factors 2116.

For example, if the external factors 2116 include the animal being transported to a different location or feedlot, the instruction 226 can include a command to increase the frequency of the sample rate due to increased stress on the animal.

As a further example, if the external factors 2116 include the animal's diet being modified to include foods with a higher risk of bloat the instruction 226 can be modified during the sampling modification decision step 2114 to increase the sampling rate while the animal is consuming the risky diet.

As yet a further example, when the external factors 2116 indicate that the stress conditions are decreasing, such as with better weather, stable environment, removal of stressing factors, or during sleep, the sampling modification decision step 2114 can modify and transmit the instruction 226 decreasing the sampling rate of the tag 102.

It has been discovered that controlling the sampling rate and other aspects of the tag 102 with the instruction 226 increases the effectiveness of the tag 102 at gathering valid, quality data while simultaneously reducing power consumption of gathering, processing, transmitting, and storing undesirable or unneeded data. As will be appreciated controlling the optical sensor 212, the motion sensor 218, the thermal sensor 220, and the tag communications module 224 of the tag 102 utilizing the instruction 226 further reduces processing requirements, storage requirements, and transmission requirements which would be needed to process, store, or transmit bad data.

The determination system 100 can initiate an alert signature detection step 2120 to determine whether alert or alarm conditions exist within the tag feature sets 228. If alert conditions are detected, the alarm step 2110 can be initiated. If alert conditions do not exist, the sampling modification decision step 2114 can be executed again.

Figure 22:
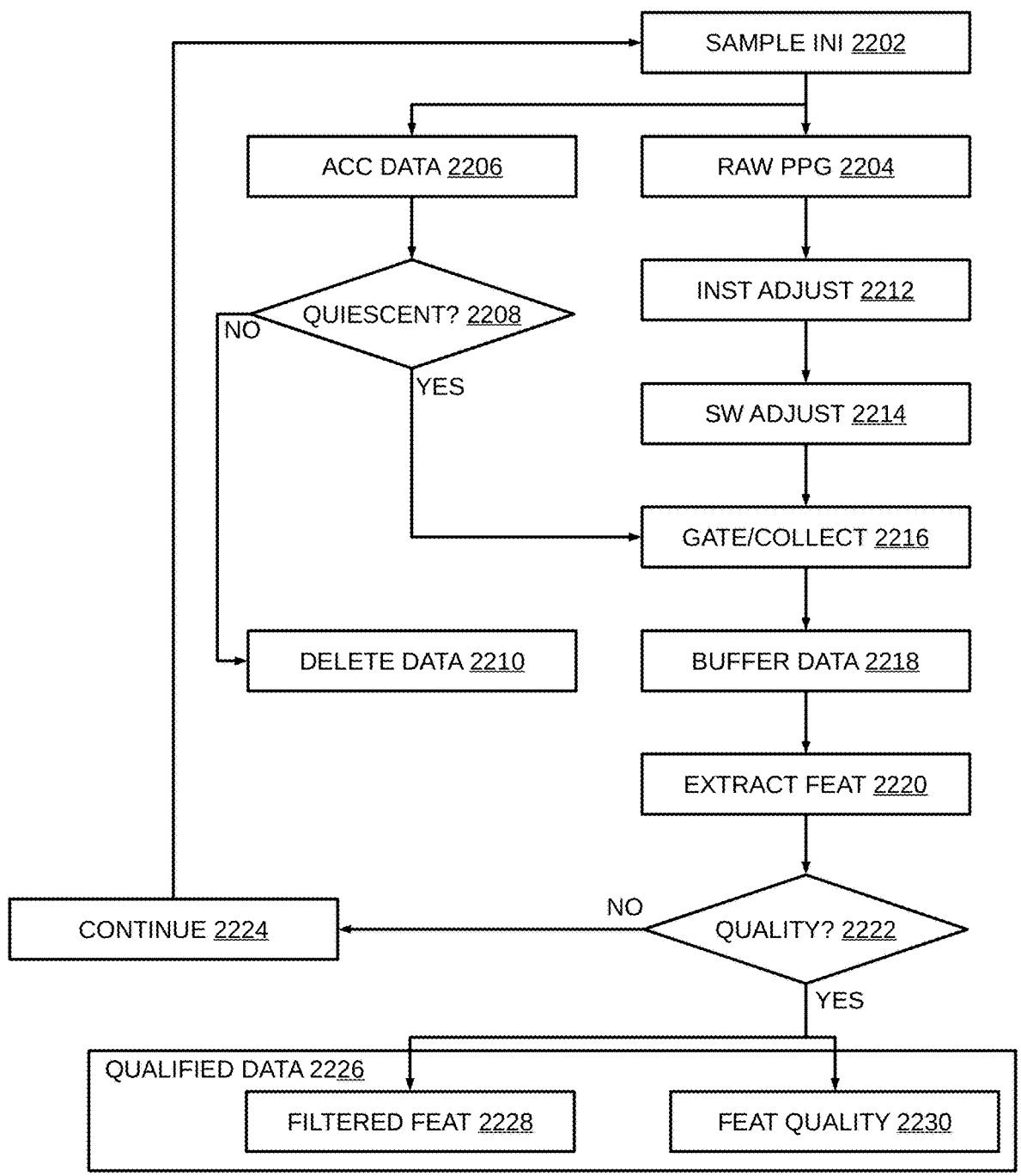
FIG. 22 is a fifth control flow for the determination system of FIG. 1.

Referring now to FIG. 22, therein is shown a fifth control flow 2200 for the determination system 100 of FIG. 1. The determination system 100 can execute a sample initiation step 2202.

It is contemplated, for example, that the sample initiation step 2202 can be triggered or started by the network 104 of FIG. 1 utilizing the instruction 226 of FIG. 2 or can be triggered by a timer within the tag 102 of FIG. 1.

The sample initiation step 2202 can initiate a raw PPG collection step 2204 and an accelerator data collection step 2206. The determination system 100 can then initiate a quiescent decision step 2208.

During the quiescent decision step 2208 the accelerator data collected during the accelerator data collection step 2206 can be analyzed for determining whether the tag 102 was quiescent, inactive, or still, during the time that the raw PPG collection step 2204 was executed.

If the determination system 100 determines that the tag 102 was not quiescent or still during the execution of the raw PPG collection step 2204, the determination system 100 can execute a delete data step 2210. Execution of the delete data step 2210 can delete the raw PPG data collected during the execution of the raw PPG collection step 2204.

As a parallel process, it is contemplated that the determination system 100 can execute the accelerator data collection step 2206 at the same time as the determination system 100 executes the raw PPG collection step 2204. The tag 102 can be adjusted once each time the tag 102 is installed in an animal in an installation adjustment step 2212.

During the installation adjustment step 2212, it is contemplated that the light source 208 of FIG. 2 would already be selected so the intensity of the light source 208 can be changed as well as the gain of the optical sensor 212 of FIG. 2. It is further contemplated that some minor improvements can be made with the selection of wavelength, for example, during the installation adjustment step 2212. The adjustments can be made for specific hair colors and hair types.

The determination system 100 can further execute a sample window adjustment step 2214. For each sampling window, herein to be understood as the time over which data is taken, many adjustments can be made to compensate for hair density, water, frost, and obscuration changes.

The sample window adjustment step 2214 can include an adjustment for the length of the sampling window, an adjustment for the automatic gain control of the optical sensor 212, an adjustment for the power of the light source 208, an adjustment for the sampling rate, and an adjustment for the filtering scheme for the data used by the determination system 100.

Unlike the installation adjustment step 2212, which is contemplated to be executed only once during the installation of the tag 102, the sample window adjustment step 2214 is contemplated and intended to be executable or executed for each of the sampling windows of the tag 102. The sample window adjustment step 2214 can be executed in parallel to the quiescent decision step 2208.

If the tag 102 is determined to be quiescent during the quiescent decision step 2208 for the sample window, the quiescent decision step 2208 can return an affirmative result and the determination system 100 can execute a gate or collect PPG data step 2216.

The gate or collect PPG data step 2216 can be executed together with a buffer data step 2218. The gate or collect PPG data step 2216 together with the buffer data step 2218 can determine when and how the raw PPG data from the raw PPG collection step 2204 is stored in memory.

For example, the raw PPG data collected during the raw PPG collection step 2204 can be collected together in a batch with many other readings from many tags 102 allowing the raw PPG data to be processed as a batch. That is, the batch of PPG data points can be processed as a batch instead of utilizing an infinite impulse response type filter.

The data buffering mechanism of the buffer data step 2218 can be implemented whether raw PPG data is gated or collected during the gate or collect PPG data step 2216. If the data buffer is full we may use a double buffer approach, which includes writing over the second half, shifting and rewriting over second half, always maintaining a full window record.

The determination system 100 can execute a feature set extraction step 2220 where the tag feature sets 228 and the network feature sets 246 are extracted as the heart rate 2004, the respiration rate 2006, the SpO2 2008, the animal temperature 2010, the arterial mean pressure 2012, the motion data 2014, the temperature data 2016, and the location data 2018, all of FIG. 20.

Illustratively, the tag feature sets 228 can include physiological components including but not limited to heart rate 2004, heart rate variability, respiration rate 2006, respiration rate variability, saturation of peripheral oxygen (SpO2)

2008, animal temperature 2010, blood urea, arterial mean pressure 2012, and physiological components associated with the sympathetic nervous system for example. It is contemplated that these physiological components can be computed and determined in accordance with the methods and procedures described herein.

Once the tag feature sets 228 and the network feature sets 246 have been extracted during the feature set extraction step 2220, the determination system 100 can execute a feature set quality determination step 2222. During the feature set quality determination step 2222, the tag feature sets 228 and the network feature sets 246 can be evaluated based on descriptive statistics, frequency content, amplitude envelope, and time series analysis.

It is further contemplated that the tag feature sets 228 and the network feature sets 246 could be evaluated based on the perfusion index of the data and ensuring data consistency within a specific range. Yet further, it is contemplated that accelerometer data or ambient light could be used to assess the quality of the tag feature sets 228 and the network feature sets 246.

If the quality of the tag feature sets 228 or the quality of the network feature sets 246 is insufficient, the feature set quality determination step 2222 can return a negative result and the determination system 100 can execute a continue collection step 2224. During the continue collection step 2224, the determination system 100 can re-execute the sample initiation step 2202 for further data collection.

If the quality of the tag feature sets 228 or the quality of the network feature sets 246 is sufficient, the feature set quality determination step 2222 can return a positive result and the determination system 100 can execute a qualified data step 2226 for providing both filtered feature sets 2228 and a feature set quality confidence level 2230.

It is contemplated, for example, that the filtered feature sets 2228 can include the tag feature sets 228 and the network feature sets 246 that were shown to have sufficient quality during the feature set quality determination step 2222. It is contemplated that the tag feature sets 228 and the network feature sets 246 not having sufficient quality can be deleted.

It is contemplated that the feature set quality confidence level 2230 can provide greater differentiability by providing an assessed confidence level of each of the feature sets. The confidence level can be generated based on one or more of the heart rate 2004, the respiration rate 2006, the SpO2 2008, the animal temperature 2010, the arterial mean pressure 2012, the motion data 2014, the temperature data 2016, and the location data 2018 falling within thresholds, or falling within statistical groupings.

It has been discovered that when the feature set quality confidence level 2230 is implemented by a third party, the results generated can be more refined and that portion of the third party algorithm will be locked with the specific optical sensor 212 used within the tag 102 ensuring the product is better positioned to retain market share once captured.

Figure 23:
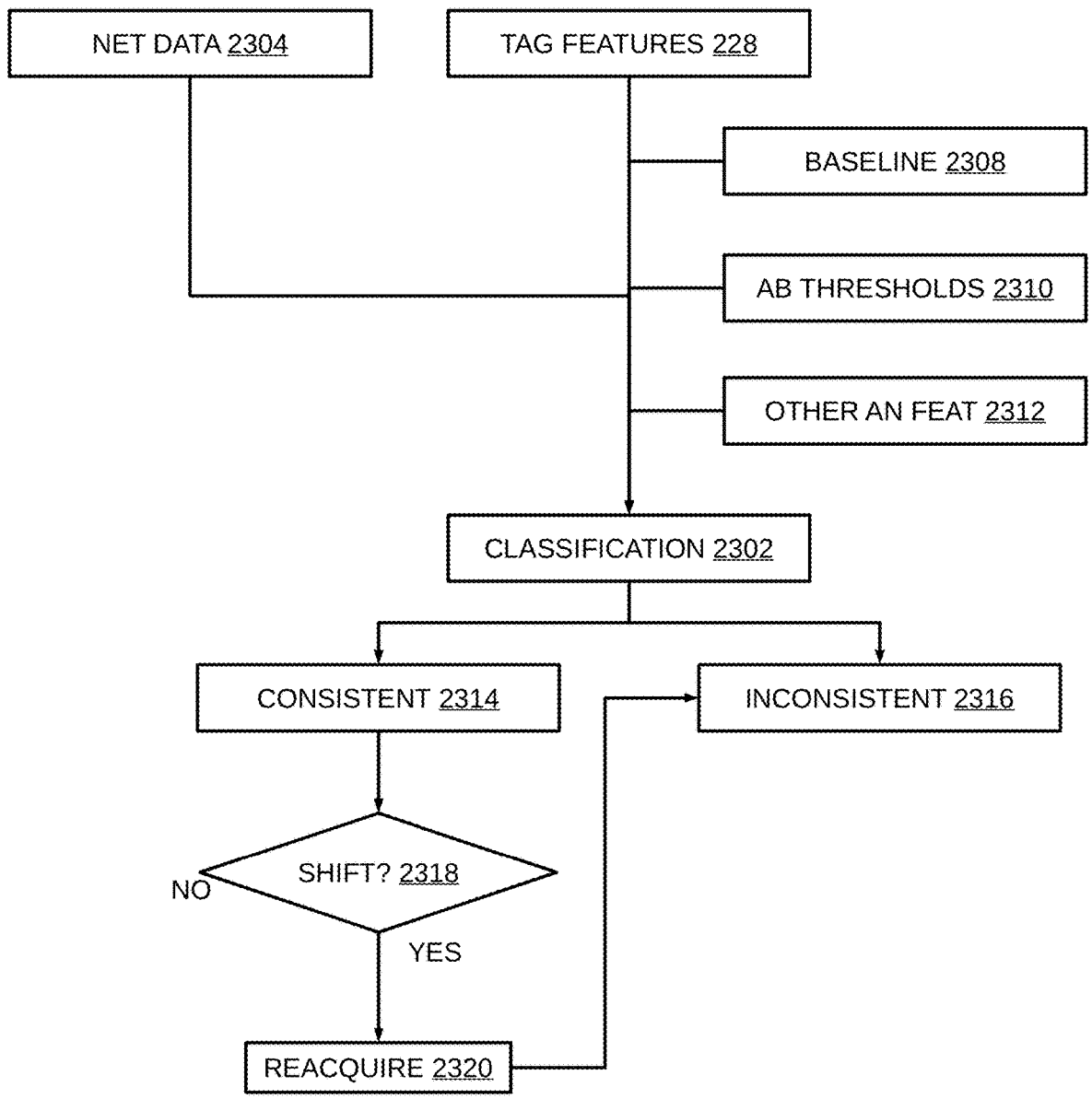
FIG. 23 is a sixth control flow for the determination system of FIG. 1.

Referring now to FIG. 23, therein is shown a sixth control flow 2300 for the determination system 100 of FIG. 1. A classification step 2302 can be executed by the determination system 100 and can receive information from multiple sources.

For example, the classification step 2302 can receive network available data 2304 including the network feature sets 246 of FIG. 2, the tag feature sets 228 of FIG. 2, an animal set baseline 2308, absolute thresholds 2310, and other animal feature sets 2312. The network available data 2304, for example, can include the time of day or other network available data including diet, and schedule.

For the purposes of this application the term "baseline" means a value or values identified as a reference for understanding data points. The baseline values can be identified from or can be derived from data acquired from the tag 102 of FIG. 1 such as the data contained within tag feature sets 228 or can be derived from data from the network 104 of FIG. 1 such as the network feature sets 246.

Illustratively, the animal set baseline 2308 can be individual statistical baselines for each of the animals and can be used by determining variance, or other statistical measurement, between the tag feature sets 228 from the animal set baseline 2308 and the animal set baseline 2308. For example, each of the animal set baseline 2308 can include baselines for each of the physiological components.

The animal set baseline 2308 can include a heart rate baseline, heart rate variability baseline, respiration rate baseline, respiration rate variability baseline, saturation of peripheral oxygen baseline, temperature baseline, blood urea baseline, and other physiological baselines derived from components associated with the sympathetic nervous system.

Continuing with this illustration, the optical sensor 212 of the tag 102 can collect the optical data from which the physiological components can be recognized and extracted. The physiological components can be compared with the animal set baseline 2308 including the baselines for each of the physiological components.

Thus, it has been discovered that the physiological components can be understood against the animal set baseline 2308 individual for each animal. This has been shown to provide many unexpected benefits including lowering treatment costs and increasing meat yields because the physiological components from each animal is collected and understood against individual baselines, which allows precise, effective, and timely diagnosis leading to more effective treatment of disease and environmental stresses.

The absolute thresholds 2310 can be signal amplitude PPG signal, signal to noise ratio, heart rate, descriptive statistics, time series, and frequency information.

As an illustrative example, the absolute thresholds 2310 can include a SpO2 reading under 85%. This can cause an alert even if it has only dropped 3% from baseline and the threshold for baseline change is 5%. This is due to the potentially noisy dataset. It is contemplated that the absolute thresholds 2310 can be a configuration setting.

The classification step 2302 can further collect information and data from the tags 102 of other animals within the vicinity, within the herd, and of the same animal type. The information and data from the tags 102 of other animals has been discovered to provide valuable insights and effectiveness at filtering out data.

The classification step 2302 can return a consistent result 2314 or an inconsistent result 2316. The consistent result 2314 can be a result congruent with the animal set baseline 2308. If the consistent result 2314 is returned by the classification step 2302, no alarm is triggered.

The inconsistent result 2316 can be returned when the tag feature sets 228 deviate from the animal set baseline 2308. When the inconsistent result 2316 is returned, an alarm can be generated.

The result from the consistent result 2314 can be used by the determination system 100 in a long term baseline shift decision step 2318. During the long term baseline shift decision step 2318, the determination system 100 can analyze the baseline and determine whether a shift can be recognized.

It is contemplated that recognizing a shift in the baseline can include identifying data points within the tag feature sets 228 based on their relationship to statistically calculated values for the individual baselines for each tag on an individual animal. Illustratively for example, a baseline shift could be recognized when data from the tag feature sets 228 falls outside of a three sigma standard deviation from a 200 point moving average for longer than a time threshold, which could be a day.

If the long term baseline shift decision step 2318 returns a negative result, the baseline has not shifted and no further action, corrective or otherwise, must be taken. If the long term baseline shift decision step 2318 returns an affirmative result, the baseline has shifted and the determination system 100 can execute a baseline acquisition step 2320 and execute the inconsistent result 2316 in order to generate an alarm for an inconsistent baseline. The baseline acquisition step 2320 is disclosed below with regard to FIG. 24.

Figure 24:
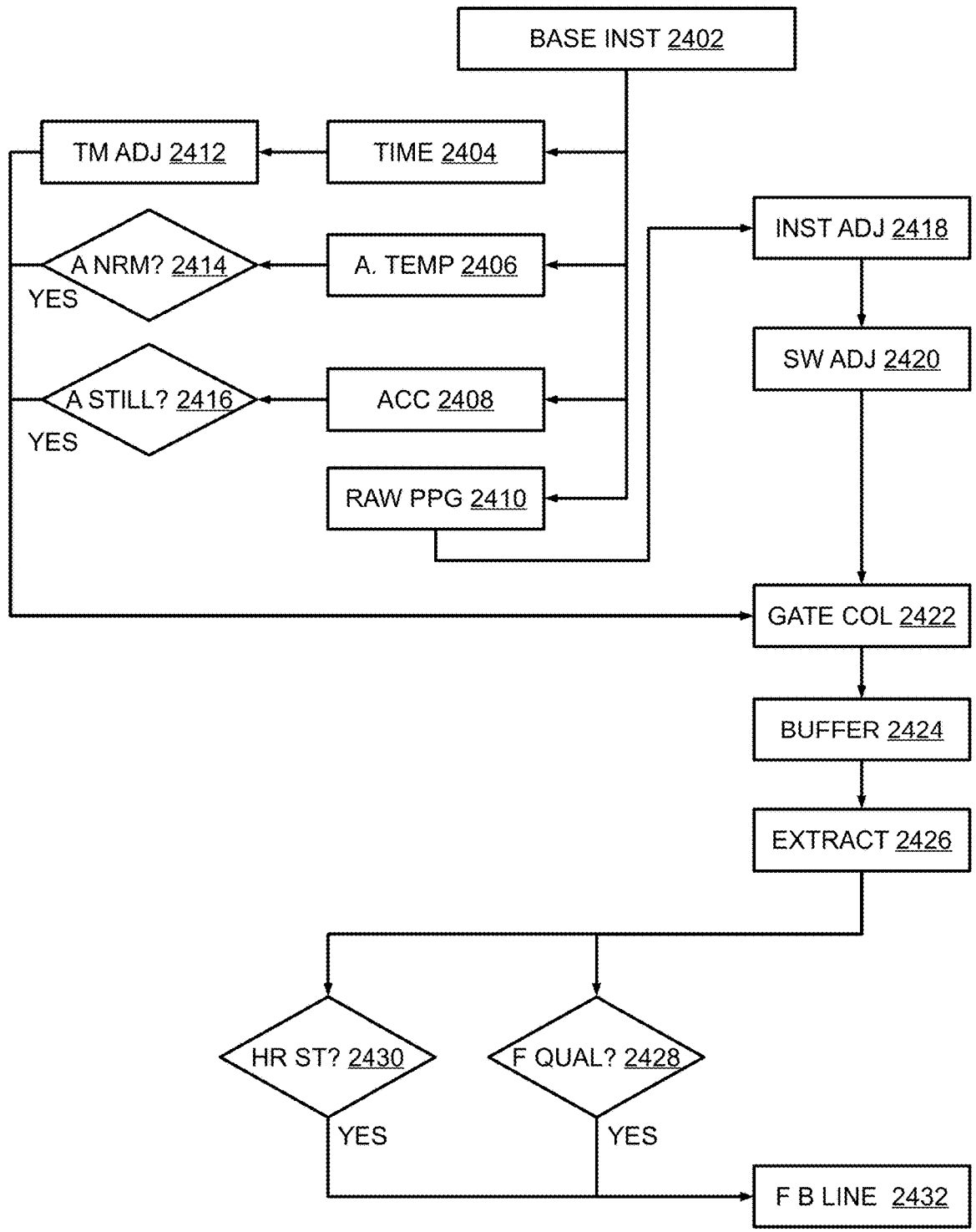
FIG. 24 is a seventh control flow for the determination system of FIG. 1.

Referring now to FIG. 24, therein is shown a seventh control flow for the determination system of FIG. 1. The seventh control flow can be the baseline acquisition step 2320 of FIG. 23.

The determination system 100 can initiate the baseline acquisition step 2320, which can be initiated with an instruction 226 of FIG. 2 from the network 104 to the tag 102 of FIG. 1 during a baseline instruction step 2402. The baseline instruction step 2402 can initiate four steps in parallel.

Illustratively, the determination system 100 can initiate a time of day step 2404, an ambient temperature step 2406, an accelerometer data step 2408, and an optical data collection step 2410. During the time of day step 2404, the determination system 100 can determine the time of day that the baseline instruction step 2402 and the baseline acquisition step 2320 is being executed, and more particularly, the exact time that the optical data was acquired by the sampling of the optical sensor 212 of FIG. 2.

It is contemplated that the time can be determined either by a clock within the tag 102 or within the network 104. The time of day step 2404 can ensure that the optical sensor 212 is only sampled during time periods in which the animal is resting or sleeping.

The resting or sleeping phase can be determined in many ways. For example, it is contemplated that sleeping animals can be assumed when the reading is taken between certain time periods, such as between 9 pm and 4 am.

In other embodiments, the time the optical sensor 212 is sampled could be combined with other data points including the location of the tag 102 within the feed lot, for example. Illustratively, when location is combined with time, the determination system 100 may recognize a repeatable and consistent point within the circadian rhythm of animals within which the optical sensor 212 can be sampled to read and retrieve the optical data including the physiological components.

As an illustrative example, the repeatable and consistent point within the circadian rhythm of an animal could be a resting or sleeping state of the animal. It is contemplated that in some implementations, sleeping or resting could be determined based on the time being within normal sleeping ranges for the animal and the animal's location is confined in a specific area of the feed lot, or is not near the feeding or watering troughs.

In yet further implementations, the determination system 100 can determine whether the animal is resting or sleeping based on movement detected by the motion sensor 218 of FIG. 2, or based on physiological components contained within the optical data collected by sampling the optical sensor 212. The physiological components can include, for example, heart rate, heart rate variability, respiration rate, respiration rate variability, saturation of peripheral oxygen, temperature, blood urea, and physiological components associated with the sympathetic nervous system to be computed.

It is contemplated that one or a combination of these physiological components can be used by the time of day step 2404 to determine whether the optical sensor 212 is sampled during a resting or sleeping cycle of the animal.

When it is determined that the optical sensor 212 is being sampled during a time when the animal is not resting or sleeping the data can be disregarded, however, the determination system 100 can execute a time adjustment step 2412 to adjust the time the optical sensor 212 is sampled in order to preserve a proper baseline. Illustratively, for example, if the readings from the optical sensor 212 are determined to be when the animal is not resting or sleeping, the time adjustment step 2412 could adjust the time the readings were taken.

It is contemplated that the time adjustment step 2412 could reschedule a reading after a time interval, such as half an hour or one hour. Alternatively, it is contemplated that the time adjustment step 2412 could reschedule the sampling of the optical sensor 212 for a time interval after a triggering event, such as, taking a reading of the optical sensor 212 one hour after the animal enters a portion of the feed lot where the animals are known or recorded as previously sleeping.

During the ambient temperature step 2406, the determination system 100 could read the ambient temperature. The ambient temperature could be read from the thermal sensor 220 of FIG. 2.

The ambient temperature of ambient temperature step 2406 could be examined to determine whether the ambient temperature detected falls within a window of thresholds during an ambient window determination step 2414. The ambient window determination step 2414 could, for example, take a temperature reading of 20° C. obtained from the thermal sensor 220 and compare this to a high temperature threshold and a low temperature threshold. If the recorded temperature is between the high temperature threshold and the low temperature threshold, the ambient window determination step 2414 can return an affirmative result otherwise the data obtained by sampling the optical sensor 212 can be disregarded upon the ambient window determination step 2414 returning a negative result.

During the accelerometer data step 2408, the determination system 100 could read the motion or acceleration of the tag 102. The motion or acceleration of the tag 102 can be detected from the accelerometer 218 of FIG. 2.

The acceleration of the accelerometer data step 2408 could be examined to determine whether the acceleration of the tag 102 detected from the accelerometer 218 falls within a window of thresholds during a stillness determination step 2416. It is contemplated that the stillness thresholds could merely be a threshold of any detected acceleration. That is if the tag 102 accelerates during the accelerometer data step 2408 the stillness determination step 2416 will return a negative result and the optical data captured from the optical sensor 212 during the time when the accelerometer data step 2408 was executed can be disregarded.

Otherwise, when the tag 102 is not determined through the accelerometer 218 to be accelerating, the stillness determination step 2416 can return an affirmative result. The optical data collection step 2410 can be executed in parallel with the accelerometer data step 2408, the ambient temperature step 2406, and the time of day step 2404.

During the optical data collection step 2410, the optical sensor 212 can be sampled to detect the optical signal including physiological parameters for obtaining or measuring heart rate, SpO2, arterial mean pressure, breath rate, core temperature estimations, or a combination thereof. The determination system 100 can further execute an installation adjustment step 2418.

During the installation adjustment step 2418, it is contemplated that the light source 208 would already be selected so the intensity of the light source 208 can be changed as well as the gain of the optical sensor 212. It is further contemplated that some minor improvements can be made with the selection of wavelength, for example, during the installation adjustment step 2418. The adjustments can be made for specific hair colors, hair types, skin pigments, skin conditions, and skin types.

The determination system 100 can further execute a sample window adjustment step 2420. For each sampling window, herein to be understood as the time over which data is taken, many adjustments can be made to compensate for hair density, water, frost, and obscuration changes.

The sample window adjustment step 2420 can include an adjustment for the length of the sampling window, an adjustment for the automatic gain control of the optical sensor 212, an adjustment for the power of the light source 208, an adjustment for the sampling rate, and an adjustment for the filtering scheme for the data used by the determination system 100.

Unlike the installation adjustment step 2418, which is contemplated to be executed only once during the installation of the tag 102, the sample window adjustment step 2420 is contemplated and intended to be executable or executed for each of the sampling windows of the tag 102. It is contemplated that when the determination system 100 recognizes that the optical data from the optical sensor 212 has been sampled during a consistent repeatable point within the circadian rhythm by the time of day step 2404 and the time adjustment step 2412, when the determination system 100 determines that the ambient temperature is within an ambient temperature window by the ambient temperature step 2406 and the ambient window determination step 2414, when the determination system 100 determines that the animal was still during the accelerometer data step 2408 and the stillness determination step 2416, or when the determination system 100 completes the sample window adjustment step 2420, a gate or collect PPG data step 2422 can be initiated.

The gate or collect PPG data step 2422 can be executed together with a buffer data step 2424. The gate or collect PPG data step 2422 together with the buffer data step 2424 can determine when and how the raw PPG data from the optical data collection step 2410 is stored in memory.

For example, the raw PPG data collected during the optical data collection step 2410 can be collected together in a batch with many other readings from many tags 102 allowing the raw PPG data to be processed as a batch. That is, the batch of PPG data points can be processed as a batch instead of utilizing an infinite impulse response type filter.

The data buffering mechanism of the buffer data step 2424 can be implemented whether raw PPG data is gated or collected during the gate or collect PPG data step 2422. If the data buffer is full a double buffer approach can be used, which includes writing over the second half, shifting and rewriting over second half, always maintaining a full window record.

The determination system 100 can execute a feature set extraction step 2426 where the tag feature sets 228 of FIG. 2 and the network feature sets 246 of FIG. 2 are extracted as the heart rate 2004, the respiration rate 2006, the SpO2 2008, the animal temperature 2010, the arterial mean pressure 2012, the motion data 2014, the temperature data 2016, and the location data 2018 all of FIG. 20.

Illustratively, the tag feature sets 228 can include physiological components including but not limited to heart rate 2004, heart rate variability, respiration rate 2006, respiration rate variability, saturation of peripheral oxygen (SpO2) 2008, animal temperature 2010, blood urea, arterial mean pressure 2012, and physiological components associated with the sympathetic nervous system for example. It is contemplated that these physiological components can be computed and determined in accordance with the methods and procedures described herein.

Once the tag feature sets 228 and the network feature sets 246 have been extracted during the feature set extraction step 2426, the determination system 100 can execute a feature set quality determination step 2428. During the feature set quality determination step 2428, the tag feature sets 228 and the network feature sets 246 can be evaluated based on descriptive statistics, frequency content, amplitude envelope, and time series analysis.

It is further contemplated that the tag feature sets 228 and the network feature sets 246 could be evaluated based on the perfusion index of the data and ensuring data consistency within a specific range. Yet further, it is contemplated that accelerometer data or ambient light could be used to assess the quality of the tag feature sets 228 and the network feature sets 246.

If the quality of the tag feature sets 228 or the quality of the network feature sets 246 is insufficient, the feature set quality determination step 2428 can return a negative result and the determination system 100 can disregard the data. If the quality of the tag feature sets 228 or the quality of the network feature sets 246 is sufficient, the feature set quality determination step 2428 can return a positive result and the determination system 100 can execute a filtered baseline step 2432.

Once the tag feature sets 228 and the network feature sets 246 have been extracted during the feature set extraction step 2426, the determination system 100 can also execute a heart rate stability determination step 2430. The heart rate stability determination step 2430 can utilize the optical data including the physiological component of heart rate over the sampling window of the optical sensor 212.

It is contemplated that the heart rate sampled could be analyzed with regard to the optical data obtained during one sampling of the optical sensor 212 for the individual animal, multiple previous heart rates of the individual animal, multiple heart rates of other animals during a similar or same sampling time, multiple previous heart rates of other animals, or a combination thereof. If the heart is determined to be stable during the heart rate stability determination step 2430 or if the quality of the tag feature sets 228 or the quality of the network feature sets 246 is sufficient the determination system 100 can execute the filtered baseline step 2432.

During the filtered baseline step 2432, the baseline for the individual tag 102 can be reestablished or reacquired. The output of the filtered baseline step 2432 is contemplated to be the output of the baseline acquisition step 2320, which can be the animal set baseline 2308 of FIG. 23.

As will be appreciated, the determination system 100 can acquire and qualify the measurement feature 229 of FIG. 2 as the animal set baseline 2308, for example of the heart rate 2004 of FIG. 20, by determining the optical data collected during the optical data collection step 2410, which is collected at a predetermined time during the natural circadian rhythm of the animal, collected during a time that the ambient temperature was within a temperature window, and collected during a time that the animal was quiescent or still. When these conditions are met, the physiological component of the optical signal, which is to be understood as the measurement feature 229, collected during the optical data collection step 2410, can be considered qualified as the animal set baseline 2308, for example.

Therefore, the time of day step 2404, the time adjustment step 2412, the ambient temperature step 2406, the ambient window determination step 2414, the accelerometer data step 2408, and the stillness determination step 2416 will be considered qualifying processes and qualifying methods for qualifying the measurement feature 229, which is the physiological component of the optical signal, as a baseline.

Once the heart rate 2004 collected during the optical data collection step 2410 is determined to be appropriate for establishing the animal set baseline 2308 for the heart rate 2004, the determination system 100 can utilize the newly collected heart rate 2004 together with previously collected data, that is known to be appropriately collected, for newly establishing the animal set baseline 2308 for the heart rate 2004. Those of ordinary skill in the art will appreciate that the physiological component of the heart rate 2004 was used as an illustrative example, and any of the other disclosed physiological components could be used to establish individual baselines for each of the physiological components and for each individual tag 102.

Thus, it has been discovered that the determination system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the determination system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

As will be appreciated, the method and system for determining a physiological condition is described and directed to improving functionality with computer networking and monitoring technologies. Specifically, it has been discovered that the disclosed systems and methods for extracting a first measurement of peripheral capillary oxygen saturation from the first optical signal, qualifying the first measurement of peripheral capillary oxygen saturation as a baseline, detecting a second optical signal with the optical sensor, extracting a second measurement of peripheral capillary oxygen saturation from the second optical signal, qualifying the second measurement of peripheral capillary oxygen saturation, and storing the second measurement of peripheral capillary oxygen saturation as a tag feature set within a computer readable media reduce power, processing, and communication requirements of computer network and monitoring technologies.

The computer network and monitoring technologies improvements stem from the fact that the system can disregard data that is not qualified leaving the determination system free to process and transmit only qualified measurement features. Further improvements to the determination system arise from storing a history including the tag feature set and previous tag feature sets within the computer readable media.

Storing the history greatly reduces costs of transferring animals between lots especially when the infrastructure is suboptimal or is not compatible between lots. Storing the history thus reduces implementation overhead.

Determining animal distress based on the difference between the second measurement of peripheral capillary oxygen saturation and the baseline, and sending an instruction to the tag, the instruction including decreasing a sampling rate of the tag based on a risk of animal distress decreasing, or increasing the sampling rate of the tag based on the risk of animal distress increasing has been discovered to reduce power consumption enabling the tags to be left on an animal over its productive life span greatly removing hurdles to implementation.

Further, it has been discovered that determining the animal distress and modifying the tags behavior based on an instruction from the network can greatly extend battery life by reducing the amount of time the tag samples. Alternatively, the tag can be more effective at detecting distress by increasing the sampling rate when appropriate. Thus, the tag can have greatly reduced power consumption when the animal distress is low and greatly increased monitoring effectiveness when the animal distress is high.

It is contemplated that a method for determining a physiological condition can include: attaching a tag to animal tissue, the tag including a light source and an optical sensor; emitting light into the animal tissue from the light source; detecting a signal of residual light from within the animal tissue with the optical sensor, the signal having a heart rate component and a saturation of peripheral oxygen component; filtering a measurement artifact out of the signal; estimating a change in core temperature based on a change in the heart rate component and the saturation of peripheral oxygen component; removing temperature changes attributable to diurnal rhythm from the change in core temperature; and triggering an alarm when the change in core temperature exceeds a temperature threshold for a length of time exceeding a time threshold.

Detecting the signal includes detecting the residual light reflected within the animal tissue based on the light source and the optical sensor being positioned on a single surface of the tag. Detecting the signal includes detecting the residual light transmitted through the animal tissue based on the light source and the optical sensor being positioned on different surfaces of the tag.

Filtering the measurement artifact includes filtering a motion artifact, an ambient light artifact, an obscurement artifact, or a combination thereof. Attaching the tag includes sandwiching a portion of the animal tissue between the tag, the tag having a post and a backing plate, the backing plate having a hole, and the post configured to extend through the animal tissue and through the hole in the backing plate.

Detecting the signal includes detecting the signal having a respiration component; and further comprising: determining respiration variability based on the respiration component of the signal; determining heart rate variability based on the heart rate component of the signal; and triggering a second alarm when the respiration variability exceeds a respiration variability threshold, the heart rate variability exceeds a heart rate variability threshold, or a combination thereof. Attaching the tag to the animal tissue includes attaching the tag in direct contact with the animal tissue or attaching the tag to the animal tissue with a spacer therebetween, an index of refraction of the spacer and an index of refraction of the animal tissue being identical or substantially similar to each other.

It is further contemplated that a non-transitory computer readable medium, useful in association with a processor, can include instructions configured to: emit light into animal tissue from a light source, the light source mounted to a tag attached to the animal tissue; detect a signal of residual light from within the animal tissue with an optical sensor on the tag, the signal having a heart rate component and a saturation of peripheral oxygen component; filter a measurement artifact out of the signal; estimate a change in core temperature based on a change in the heart rate component and the saturation of peripheral oxygen component; remove temperature changes attributable to diurnal rhythm from the change in core temperature; and trigger an alarm when the change in core temperature exceeds a temperature threshold for a length of time exceeding a time threshold. The instructions configured to detect the signal include instructions configured to detect the residual light reflected within the animal tissue based on the light source and the optical sensor being positioned on a single surface of the tag.

The instructions configured to detect the signal include instructions configured to detect the residual light transmitted through the animal tissue based on the light source and the optical sensor being positioned on different surfaces of the tag. The instructions configured to filter the measurement artifact include instructions configured to filter a motion artifact, an ambient light artifact, an obscurement artifact, or a combination thereof.

The instructions configured to detect the signal include instructions configured to detect the signal having a respiration component; and further instructions could include instructions configured to: determine respiration variability based on the respiration component of the signal; determine heart rate variability based on the heart rate component of the signal; and trigger a second alarm when the respiration variability exceeds a respiration variability threshold, the heart rate variability exceeds a heart rate variability threshold, or a combination thereof. Further instructions can include instructions configured to transmit the signal from the tag to a network.

It is yet further contemplated that a physiological condition determination system can include: a tag configured to attach to animal tissue, the tag including a light source and an optical sensor, the light source configured to emit light into the animal tissue, the optical sensor configured to detect a signal of residual light from within the animal tissue, and the signal having a heart rate component and a saturation of peripheral oxygen component; and a processor configured to filter measurement artifacts out of the signal, estimate a change in core temperature based on a change in the heart rate component and the saturation of peripheral oxygen component, remove temperature changes attributable to diurnal rhythm from the change in core temperature, and trigger an alarm when the change in core temperature exceeds a temperature threshold for a length of time exceeding a time threshold.

The optical sensor is configured to detect the residual light reflected within the animal tissue based on the light source and the optical sensor being positioned on a single surface of the tag. The optical sensor is configured to detect the residual light transmitted through the animal tissue based on the light source and the optical sensor being positioned on different surfaces of the tag. The processor is configured to filter motion artifacts, and ambient light artifacts, and obscurement artifacts.

The tag is configured to sandwich a portion of the animal tissue between the tag, the tag having a post and a backing plate, the backing plate having a hole, and the post configured to extend through the animal tissue and through the hole in the backing plate. The optical sensor is configured to detect the signal having a respiration component; and the processor is configured to: determine respiration variability based on the respiration component of the signal; determine heart rate variability based on the heart rate component of the signal; and trigger a second alarm when the respiration variability exceeds a respiration variability threshold, the heart rate variability exceeds a heart rate variability threshold, or a combination thereof. The tag is configured to attach to the animal tissue with direct contact or to the animal tissue with a spacer therebetween, an index of refraction of the spacer and an index of refraction of the animal tissue being identical or substantially similar to each other.

It is further contemplated that a method for determining a physiological condition can include: attaching a tag to animal tissue, the tag including a light source and an optical sensor; emitting light into the animal tissue from the light source; detecting a signal of residual light from within the animal tissue with the optical sensor, the signal having a first physiological component and a second physiological component; filtering a measurement artifact out of the signal; estimating a change in temperature based on a change in the first physiological component and the second physiological component; removing temperature changes attributable to diurnal rhythm from the change in temperature; and triggering an alarm when the change in temperature exceeds a temperature threshold for a length of time exceeding a time threshold.

Estimating the change in temperature includes estimating a change in core temperature. Attaching the tag includes attaching the tag having the light source comprised of a light emitting diode.

Estimating the change in temperature includes estimating the change in temperature based on the first physiological component being a heart rate component and the second physiological component being a saturation of peripheral oxygen component. Attaching the tag includes sandwiching a portion of the animal tissue between the tag, the tag having a post and a backing plate, the backing plate having a hole, and the post being configured to extended through the animal tissue and through the hole in the backing plate.

Attaching the tag includes attaching the tag with the light source and the optical sensor being positioned on a surface of the post. Attaching the tag includes attaching the tag having a tag body, and the light source and the optical sensor being positioned on a surface of the tag body. Attaching the tag includes attaching the tag having a tag body, the light source being positioned on a surface of the post, and the optical sensor being positioned on a surface of the tag body.

It is further contemplated that a method for determining a physiological condition can include: attaching a tag to animal tissue, the tag including a light source and an optical sensor; emitting light into the animal tissue from the light source; detecting a signal of residual light from within the animal tissue with the optical sensor, the signal having a heart rate component and a saturation of peripheral oxygen component; filtering a measurement artifact out of the signal; estimating a change in core temperature based on a change in the heart rate component and the saturation of peripheral oxygen component; removing temperature changes attributable to diurnal rhythm from the change in core temperature; and triggering an alarm when the change in core temperature exceeds a temperature threshold for a length of time exceeding a time threshold.

Detecting the signal includes detecting the residual light reflected within the animal tissue based on the light source and the optical sensor being positioned on a single surface of the tag. Detecting the signal includes detecting the residual light transmitted through the animal tissue based on the light source and the optical sensor being positioned on different surfaces of the tag.

Filtering the measurement artifact includes filtering a motion artifact, an ambient light artifact, an obscurement artifact, or a combination thereof. Attaching the tag includes sandwiching a portion of the animal tissue between the tag, the tag having a post and a backing plate, the backing plate having a hole, and the post configured to extend through the animal tissue and through the hole in the backing plate.

Detecting the signal includes detecting the signal having a respiration component; and further includes: determining respiration variability based on the respiration component of the signal; determining heart rate variability based on the heart rate component of the signal; and triggering a second alarm when the respiration variability exceeds a respiration variability threshold, the heart rate variability exceeds a heart rate variability threshold, or a combination thereof. Attaching the tag to the animal tissue includes attaching the tag in direct contact with the animal tissue or attaching the tag to the animal tissue with a spacer therebetween, an index of refraction of the spacer and an index of refraction of the animal tissue being identical or substantially similar to each other.

It is further contemplated that a non-transitory computer readable medium, useful in association with a processor, can include instructions configured to: emit light into animal tissue from a light source, the light source mounted to a tag attached to the animal tissue; detect a signal of residual light from within the animal tissue with an optical sensor on the tag, the signal having a heart rate component and a saturation of peripheral oxygen component; filter a measurement artifact out of the signal; estimate a change in core temperature based on a change in the heart rate component and the saturation of peripheral oxygen component; remove temperature changes attributable to diurnal rhythm from the change in core temperature; and trigger an alarm when the change in core temperature exceeds a temperature threshold for a length of time exceeding a time threshold.

The instructions configured to detect the signal include instructions configured to detect the residual light reflected within the animal tissue based on the light source and the optical sensor being positioned on a single surface of the tag. The instructions configured to detect the signal include instructions configured to detect the residual light transmitted through the animal tissue based on the light source and the optical sensor being positioned on different surfaces of the tag. The instructions configured to filter the measurement artifact include instructions configured to filter a motion artifact, an ambient light artifact, an obscurement artifact, or a combination thereof. The instructions configured to detect the signal include instructions configured to detect the signal having a respiration component; and further includes instructions configured to: determine respiration variability based on the respiration component of the signal; determine heart rate variability based on the heart rate component of the signal; and trigger a second alarm when the respiration variability exceeds a respiration variability threshold, the heart rate variability exceeds a heart rate variability threshold, or a combination thereof. Further instructions can include instructions configured to transmit the signal from the tag to a network.

A physiological condition determination system can include: a tag configured to attach to animal tissue, the tag including a light source and an optical sensor, the light source configured to emit light into the animal tissue, the optical sensor configured to detect a signal of residual light from within the animal tissue, and the signal having a heart rate component and a saturation of peripheral oxygen component; and a processor configured to filter measurement artifacts out of the signal, estimate a change in core temperature based on a change in the heart rate component and the saturation of peripheral oxygen component, remove temperature changes attributable to diurnal rhythm from the change in core temperature, and trigger an alarm when the change in core temperature exceeds a temperature threshold for a length of time exceeding a time threshold.

The optical sensor is configured to detect the residual light reflected within the animal tissue based on the light source and the optical sensor being positioned on a single surface of the tag. The optical sensor is configured to detect the residual light transmitted through the animal tissue based on the light source and the optical sensor being positioned on different surfaces of the tag.

The processor is configured to filter motion artifacts, and ambient light artifacts, and obscurement artifacts. The tag is configured to sandwich a portion of the animal tissue between the tag, the tag having a post and a backing plate, the backing plate having a hole, and the post configured to extend through the animal tissue and through the hole in the backing plate.

The optical sensor is configured to detect the signal having a respiration component; and the processor is configured to: determine respiration variability based on the respiration component of the signal; determine heart rate variability based on the heart rate component of the signal; and trigger a second alarm when the respiration variability exceeds a respiration variability threshold, the heart rate variability exceeds a heart rate variability threshold, or a combination thereof. The tag is configured to attach to the animal tissue with direct contact or to the animal tissue with a spacer therebetween, an index of refraction of the spacer and an index of refraction of the animal tissue being identical or substantially similar to each other.

A method for determining a physiological condition can include: attaching a tag to animal tissue, the tag including a light source and an optical sensor; emitting light into the animal tissue from the light source; detecting a signal of residual light from within the animal tissue with the optical sensor, the signal having a first physiological component and a second physiological component; filtering a measurement artifact out of the signal; estimating a change in temperature based on a change in the first physiological component and the second physiological component; removing temperature changes attributable to diurnal rhythm from the change in temperature; and triggering an alarm when the change in temperature exceeds a temperature threshold for a length of time exceeding a time threshold.

Estimating the change in temperature includes estimating a change in core temperature. Attaching the tag includes attaching the tag having the light source comprised of a light emitting diode.

Estimating the change in temperature includes estimating the change in temperature based on the first physiological component being a heart rate component and the second physiological component being a saturation of peripheral oxygen component. Attaching the tag includes sandwiching a portion of the animal tissue between the tag, the tag having a post and a backing plate, the backing plate having a hole, and the post being configured to extended through the animal tissue and through the hole in the backing plate.

Attaching the tag includes attaching the tag with the light source and the optical sensor being positioned on a surface of the post. Attaching the tag includes attaching the tag having a tag body, and the light source and the optical sensor being positioned on a surface of the tag body. Attaching the tag includes attaching the tag having a tag body, the light source being positioned on a surface of the post, and the optical sensor being positioned on a surface of the tag body.

A method for determining a physiological condition can include: attaching a tag to animal tissue, the tag including a light source, an optical sensor, a motion sensor, a thermal sensor, a tag communications module, and computer readable media, the motion sensor providing motion data, the thermal sensor providing temperature data of an ambient temperature surrounding the tag, and the tag communications module providing location data of the tag; emitting light into the animal tissue from the light source; detecting an optical signal of residual light from within the animal tissue with the optical sensor; extracting saturation of peripheral oxygen and heart rate from the optical signal; qualifying the saturation of peripheral oxygen with the motion data, the temperature data, and the heart rate; storing the saturation of peripheral oxygen, the heart rate, the motion data, and the temperature data as a tag feature set within the computer readable media; storing a history including the tag feature set and previous tag feature sets within the computer readable media; determining animal distress based on the optical signal, the motion data, and the temperature data; sending an instruction to the tag, the instruction decrease a sampling rate of the tag based on the risk of animal distress decreasing, or increase the sampling rate of the tag based on the risk of animal distress increasing.

Detecting the signal includes detecting the residual light reflected within the animal tissue based on the light source and the optical sensor being positioned on a single surface of the tag, the residual light transmitted through the animal tissue based on the light source and the optical sensor being positioned on different surfaces of the tag, or a combination thereof. The method can further include: estimating a change in core temperature based on a change in the heart rate and the saturation of peripheral oxygen; removing temperature changes attributable to diurnal rhythm from the change in core temperature; and triggering an alarm when the change in core temperature exceeds a temperature threshold for a length of time exceeding a time threshold.

Determining animal distress includes: determining inflammation based on detecting a drop in the saturation of peripheral oxygen and an increase in the core temperature; determining bloat based on detecting a dangerous drop in the saturation of peripheral oxygen alone or in combination with detecting an increase in the heart rate; determining heat stress based on detecting a rapid respiratory cycle impacting both the heart rate and the saturation of peripheral oxygen, an increase in the core temperature, and an increase in the ambient temperature; determining illnesses based on a reduction in the motion data indicating lethargy or depression along with a rise in the core temperature; determining stressed based on detecting variability in the heart rate, and variability in the motion data; and determining calving based on detecting cycles in the saturation of peripheral oxygen, the heart rate, and the motion data. Qualifying the saturation of peripheral oxygen includes deleting the saturation of peripheral oxygen based on the motion data indicating movement, based on the location data indicating the position of the tag within a feeding trough, or a combination thereof.

Attaching the tag includes sandwiching a portion of the animal tissue between the tag, the tag having a post and a backing plate, the backing plate having a hole, and the post configured to extend through the animal tissue and through the hole in the backing plate. Detecting the optical signal includes detecting the optical signal having a respiration component; and further including: determining respiration variability based on the respiration component of the signal; determining heart rate variability based on the heart rate component of the signal; and triggering a second alarm when the respiration variability exceeds a respiration variability threshold, the heart rate variability exceeds a heart rate variability threshold, or a combination thereof. Attaching the tag to the animal tissue includes attaching the tag in direct contact with the animal tissue or attaching the tag to the animal tissue with a spacer therebetween, an index of refraction of the spacer and an index of refraction of the animal tissue being identical or substantially similar to each other.

A non-transitory computer readable medium, useful in association with a processor, can include instructions configured to: detect motion data, temperature data, and location data from a tag attached to animal tissue, the tag including a light source, an optical sensor, a motion sensor for detecting the motion data, a thermal sensor for detecting the temperature data, a tag communications module for detecting the location data, and computer readable media, and the temperature data being an ambient temperature surrounding the tag; emit light into the animal tissue from the light source;

detect an optical signal of residual light from within the animal tissue with the optical sensor;

extract saturation of peripheral oxygen and heart rate from the optical signal; qualify the saturation of peripheral oxygen with the motion data, the temperature data, and the heart rate; store the saturation of peripheral oxygen, the heart rate, the motion data, and the temperature data as a tag feature set within the computer readable media; store a history including the tag feature set and previous tag feature sets within the computer readable media; determine animal distress based on the optical signal, the motion data, and the temperature data; send an instruction to the tag, the instruction decrease a sampling rate of the tag based on the risk of animal distress decreasing, or increase the sampling rate of the tag based on the risk of animal distress increasing.

The instructions configured to detect the signal include instructions configured to detect the residual light reflected within the animal tissue based on the light source and the optical sensor being positioned on a single surface of the tag, the residual light transmitted through the animal tissue based on the light source and the optical sensor being positioned on different surfaces of the tag, or a combination thereof. Further including instructions configured to: estimate a change in core temperature based on a change in the heart rate and the saturation of peripheral oxygen; remove temperature changes attributable to diurnal rhythm from the change in core temperature; and trigger an alarm when the change in core temperature exceeds a temperature threshold for a length of time exceeding a time threshold.

The instructions configured to determine animal distress further includes instructions configured to: determine inflammation based on detecting a drop in the saturation of peripheral oxygen and an increase in the core temperature; determine bloat based on detecting a dangerous drop in the saturation of peripheral oxygen alone or in combination with detecting an increase in the heart rate; determine heat stress based on detecting a rapid respiratory cycle impacting both the heart rate and the saturation of peripheral oxygen, an increase in the core temperature, and an increase in the ambient temperature; determine illnesses based on a reduction in the motion data indicating lethargy or depression along with a rise in the core temperature; determine stressed based on detecting variability in the heart rate, and variability in the motion data; and determine calving based on detecting cycles in the saturation of peripheral oxygen, the heart rate, and the motion data. The instructions configured to qualify the saturation of peripheral oxygen includes instructions configured to delete the saturation of peripheral oxygen based on the motion data indicating movement, based on the location data indicating the position of the tag within a feeding trough, or a combination thereof.

The instructions configured to detect the optical signal includes instructions configured to detect the optical signal having a respiration component; and can further include instructions configured to: determine respiration variability based on the respiration component of the signal; determine heart rate variability based on the heart rate component of the signal; and trigger a second alarm when the respiration variability exceeds a respiration variability threshold, the heart rate variability exceeds a heart rate variability threshold, or a combination thereof.

A physiological condition determination system can include: a tag configured to attach to animal tissue, the tag including a light source, an optical sensor, a motion sensor, a thermal sensor, a tag communications module, and computer readable media, the motion sensor providing motion data, the thermal sensor providing temperature data of an ambient temperature surrounding the tag, the tag communications module providing location data of the tag, emit light into the animal tissue from the light source, and detect an optical signal of residual light from within the animal tissue with the optical sensor; and a processor configured to: extract saturation of peripheral oxygen and heart rate from the optical signal; qualify the saturation of peripheral oxygen with the motion data, the temperature data, and the heart rate, store the saturation of peripheral oxygen, the heart rate, the motion data, and the temperature data as a tag feature set within the computer readable media; store a history including the tag feature set and previous tag feature sets within the computer readable media, determine animal distress based on the optical signal, the motion data, and the temperature data, and send an instruction to the tag, the instruction decrease a sampling rate of the tag based on the risk of animal distress decreasing, or increase the sampling rate of the tag based on the risk of animal distress increasing.

The optical sensor is configured to detect the residual light reflected within the animal tissue based on the light source and the optical sensor being positioned on a single surface of the tag, the residual light transmitted through the animal tissue based on the light source and the optical sensor being positioned on different surfaces of the tag, or a combination thereof. The processor is configured to: estimate a change in core temperature based on a change in the heart rate and the saturation of peripheral oxygen; remove temperature changes attributable to diurnal rhythm from the change in core temperature; and trigger an alarm when the change in core temperature exceeds a temperature threshold for a length of time exceeding a time threshold.

The processor is configured to: determine inflammation based on detecting a drop in the saturation of peripheral oxygen and an increase in the core temperature; determine bloat based on detecting a dangerous drop in the saturation of peripheral oxygen alone or in combination with detecting an increase in the heart rate; determine heat stress based on detecting a rapid respiratory cycle impacting both the heart rate and the saturation of peripheral oxygen, an increase in the core temperature, and an increase in the ambient temperature; determine illnesses based on a reduction in the motion data indicating lethargy or depression along with a rise in the core temperature; determine stressed based on detecting variability in the heart rate, and variability in the motion data; and determine calving based on detecting cycles in the saturation of peripheral oxygen, the heart rate, and the motion data. The processor configured to qualify the saturation of peripheral oxygen includes the processor configured to delete the saturation of peripheral oxygen based on the motion data indicating movement, based on the location data indicating the position of the tag within a feeding trough, or a combination thereof.

The tag is configured to sandwich a portion of the animal tissue between the tag, the tag having a post and a backing plate, the backing plate having a hole, the post configured to extend through the animal tissue and through the hole in the backing plate, the tag attached in direct contact with the animal tissue or the tag attached to the animal tissue with a spacer therebetween, an index of refraction of the spacer and an index of refraction of the animal tissue being identical or substantially similar to each other.

What is claimed is:

1. A method for determining a physiological condition comprising:
    attaching a tag to animal tissue of an animal, the tag including a motion sensor, a light source, and an optical sensor;
    emitting light into the animal tissue from the light source;
    detecting a first optical signal of residual light from within the animal tissue with the optical sensor;
    extracting a first measurement of peripheral capillary oxygen saturation from the first optical signal;
    qualifying the first measurement of peripheral capillary oxygen saturation as a baseline based on motion data from the motion sensor;
    detecting a second optical signal with the optical sensor;
    extracting a second measurement of peripheral capillary oxygen saturation from the second optical signal;
    qualifying the second measurement of peripheral capillary oxygen saturation;
    storing the second measurement of peripheral capillary oxygen saturation as a tag feature set within a computer readable medium;
    storing a history including the tag feature set and previous tag feature sets within the computer readable medium;
    determining animal distress based at least on a difference between the second measurement of peripheral capillary oxygen saturation and the baseline;
    sending a first instruction to the tag, the first instruction including decreasing a sampling rate of the tag based on a risk of animal distress decreasing, or increasing the sampling rate of the tag based on the risk of animal distress increasing; and
    sending a second instruction to the tag, the second instruction including increasing the sampling rate based on a diet of the animal being changed, and not sending the second instruction based on the diet of the animal not being changed.

2. The method of claim 1 wherein the tag further comprises a thermal sensor, a tag communications module, and the computer readable medium, the motion sensor providing the motion data, the thermal sensor providing temperature data of an ambient temperature surrounding the tag, and the tag communications module providing location data of the tag.

3. The method of claim 1 further comprising detecting ambient temperature; and wherein qualifying the second measurement of peripheral capillary oxygen saturation includes qualifying the second measurement of peripheral capillary oxygen saturation with the motion data, the ambient temperature, or a combination thereof.

4. The method of claim 1 further comprising extracting a heart rate from the second optical signal, and wherein qualifying the second measurement of peripheral capillary oxygen saturation includes qualifying the second measurement of peripheral capillary oxygen saturation with the heart rate.

5. The method of claim 1 further comprising:
estimating a change in core temperature based on a change in a heart rate and the second measurement of peripheral capillary oxygen saturation;
removing temperature changes attributable to diurnal rhythm from the change in core temperature; and
triggering an alarm when the change in core temperature exceeds a temperature threshold for a length of time exceeding a time threshold.

6. The method of claim 5 wherein determining animal distress includes:
determining inflammation based on detecting a drop in the second measurement of peripheral capillary oxygen saturation and an increase in core temperature;
determining bloat based on detecting the drop in the second measurement of peripheral capillary oxygen saturation alone or in combination with detecting an increase in heart rate;
determining heat stress based on detecting a rapid respiratory cycle impacting both the heart rate and the second measurement of peripheral capillary oxygen saturation, the increase in core temperature, and an increase in ambient temperature;
determining illnesses based on a reduction in the motion data indicating lethargy or depression along with the increase in core temperature;
determining stress based on detecting variability in the heart rate and in the motion data; and
determining calving based on detecting cycles in the second measurement of peripheral capillary oxygen saturation, the heart rate, and the motion data.

7. The method of claim 1 wherein qualifying the second measurement of peripheral capillary oxygen saturation includes deleting the second measurement of peripheral capillary oxygen saturation based on the motion data indicating movement, based on location data indicating a position of the tag within a feeding trough, or a combination thereof.

8. A non-transitory computer readable medium, useful in association with a processor, including instructions configured to:
detect a first optical signal of residual light from a tag attached to animal tissue of an animal, the tag including a motion sensor, a light source, and an optical sensor, the light source for emitting light into the animal tissue, and the optical sensor for detecting the first optical signal;
extract a first measurement of peripheral capillary oxygen saturation from the first optical signal;
qualify the first measurement of peripheral capillary oxygen saturation as a baseline based on motion data from the motion sensor;
detect a second optical signal with the optical sensor;
extract a second measurement of peripheral capillary oxygen saturation from the second optical signal;
qualify the second measurement of peripheral capillary oxygen saturation;
store the second measurement of peripheral capillary oxygen saturation as a tag feature set within the computer readable medium;
store a history including the tag feature set and previous tag feature sets within the computer readable medium;
determine animal distress based on a difference between the second measurement of peripheral capillary oxygen saturation and the baseline;
send a first instruction to the tag, the first instruction including decreasing a sampling rate of the tag based on a risk of animal distress decreasing, or increasing the sampling rate of the tag based on the risk of animal distress increasing; and
send a second instruction to the tag, the second instruction including increasing the sampling rate based on a diet of the animal being changed, and not sending the second instruction based on the diet of the animal not being changed.

9. The computer readable medium of claim 8 further comprising instructions configured to detect a temperature data of an ambient temperature surrounding the tag from a thermal sensor, and location data of the tag from a tag communications module.

10. The computer readable medium of claim 8 further comprising instructions configured to detect ambient temperature around the tag; and wherein the instructions configured to qualify the second measurement of peripheral capillary oxygen saturation includes instructions configured to qualify the second measurement of peripheral capillary oxygen saturation with the motion data, the ambient temperature, or a combination thereof.

11. The computer readable medium of claim 8 further comprising instructions configured to extract a heart rate from the second optical signal; and wherein the instructions configured to qualify the second measurement of peripheral capillary oxygen saturation includes instructions configured to qualify the second measurement of peripheral capillary oxygen saturation with the heart rate.

12. The computer readable medium of claim 8 further comprising instructions configured to:
estimate a change in core temperature based on a change in heart rate and the second measurement of peripheral capillary oxygen saturation;
remove temperature changes attributable to diurnal rhythm from the change in core temperature; and
trigger an alarm when the change in core temperature exceeds a temperature threshold for a length of time exceeding a time threshold.

13. The computer readable medium of claim 12 wherein the instructions configured to determine animal distress further includes instructions configured to:
determine inflammation based on detecting a drop in the second measurement of peripheral capillary oxygen saturation and an increase in core temperature;

determine bloat based on detecting the drop in the second measurement of peripheral capillary oxygen saturation alone or in combination with detecting an increase in heart rate;

determine heat stress based on detecting a rapid respiratory cycle impacting both a heart rate and the second measurement of peripheral capillary oxygen saturation, the increase in core temperature, and an increase in ambient temperature;

determine illnesses based on a reduction in the motion data indicating lethargy or depression along with the increase in core temperature;

determine stress based on detecting variability in the heart rate and in the motion data; and determine calving based on detecting cycles in the second measurement of peripheral capillary oxygen saturation, the heart rate, and the motion data.

14. The computer readable medium of claim 8 wherein the instructions configured to qualify the second measurement of peripheral capillary oxygen saturation includes instructions configured to delete the second measurement of peripheral capillary oxygen saturation based on the motion data indicating movement, based on location data indicating a position of the tag within a feeding trough, or a combination thereof.

15. A physiological condition determination system comprising:

a tag configured to attach to animal tissue of an animal, the tag including a motion sensor, a light source and an optical sensor, the light source configured to emit light into the animal tissue, and the optical sensor configured to detect a first optical signal and a second optical signal of residual light from within the animal tissue; and a processor configured to:
extract a first measurement of peripheral capillary oxygen saturation from the first optical signal;
qualify the first measurement of peripheral capillary oxygen saturation as a baseline based on motion data from the motion sensor;
extract a second measurement of peripheral capillary oxygen saturation from the second optical signal;
qualify the second measurement of peripheral capillary oxygen saturation;
store the second measurement of peripheral capillary oxygen saturation as a tag feature set within a computer readable medium;
store a history including the tag feature set and previous tag feature sets within the computer readable medium;
determine animal distress based on a difference between the second measurement of peripheral capillary oxygen saturation and the baseline;
send a first instruction to the tag, the first instruction including decreasing a sampling rate of the tag based on a risk of animal distress decreasing, or increasing the sampling rate of the tag based on the risk of animal distress increasing; and
send a second instruction to the tag, the second instruction including increasing the sampling rate based on a diet of the animal being changed, and not sending the second instruction based on the diet of the animal not being changed.

16. The system of claim 15 wherein the tag includes a thermal sensor and a tag communications module, the motion sensor providing the motion data, the thermal sensor providing temperature data of an ambient temperature surrounding the tag, and the tag communications module providing location data of the tag.

17. The system of claim 16 wherein the processor is further configured to qualify the second measurement of peripheral capillary oxygen saturation with the motion data, the ambient temperature, or a combination thereof.

18. The system of claim 15 wherein the processor is further configured to extract a heart rate from the second optical signal and qualify the second measurement of peripheral capillary oxygen saturation with the heart rate.

19. The system of claim 15 wherein the processor is further configured to delete the second measurement of peripheral capillary oxygen saturation based on the motion data indicating movement, based on a location data indicating a position of the tag within a feeding trough, or a combination thereof.

20. The system of claim 15 wherein the tag is configured to sandwich a portion of the animal tissue between the tag, the tag having a post and a backing plate, the backing plate having a hole, the post configured to extend through the animal tissue and through the hole in the backing plate, the tag attached to the animal tissue with a sealant or an optically clear encapsulation in direct contact with both the animal tissue and the optical sensor, the sealant or the optically clear encapsulation having an index of refraction identical or substantially similar to an animal tissue index of refraction.

* * * * *